(12) United States Patent
Mauro et al.

(10) Patent No.: US 9,359,616 B2
(45) Date of Patent: Jun. 7, 2016

(54) RIBOSOMAL POLYNUCLEOTIDES AND RELATED EXPRESSION SYSTEMS

(71) Applicant: The Scripps Research Institute, La Jolla, CA (US)

(72) Inventors: Vincent P. Mauro, La Jolla, CA (US); Luke Burman, La Jolla, CA (US); Gerald M. Edelman, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 276 days.

(21) Appl. No.: 13/899,284

(22) Filed: May 21, 2013

(65) Prior Publication Data

US 2013/0309682 A1 Nov. 21, 2013

Related U.S. Application Data

(60) Provisional application No. 61/649,453, filed on May 21, 2012, provisional application No. 61/778,194, filed on Mar. 12, 2013.

(51) Int. Cl.
*C12Q 1/68* (2006.01)
*C12N 15/85* (2006.01)
*C12N 15/67* (2006.01)

(52) U.S. Cl.
CPC ............... *C12N 15/85* (2013.01); *C12N 15/67* (2013.01)

(58) Field of Classification Search
CPC ................................. C12N 15/67; C12N 15/85
USPC ......................................................... 536/24.3
See application file for complete search history.

(56) References Cited

U.S. PATENT DOCUMENTS

| | | |
|---|---|---|
| 4,469,863 A | 9/1984 | Ts'O et al. |
| 5,536,821 A | 7/1996 | Agrawal et al. |
| 5,541,306 A | 7/1996 | Agrawal et al. |
| 5,614,622 A | 3/1997 | Iyer et al. |
| 5,637,683 A | 6/1997 | Usher et al. |
| 5,637,684 A | 6/1997 | Cook et al. |
| 5,700,922 A | 12/1997 | Cook |
| 5,717,083 A | 2/1998 | Cook et al. |
| 5,719,262 A | 2/1998 | Buchardt et al. |
| 5,739,308 A | 4/1998 | Kandimalla et al. |
| 5,739,314 A | 4/1998 | Roy et al. |
| 5,773,601 A | 6/1998 | Agrawal |
| 5,886,165 A | 3/1999 | Kandimalla et al. |
| 5,929,226 A | 7/1999 | Padmapriya et al. |
| 5,955,599 A | 9/1999 | Iyer et al. |
| 5,962,674 A | 10/1999 | Iyer et al. |
| 5,965,408 A | 10/1999 | Short |
| 5,977,296 A | 11/1999 | Nielsen et al. |
| 6,117,992 A | 9/2000 | Iyer |
| 6,140,482 A | 10/2000 | Iyer et al. |
| 6,455,308 B1 | 9/2002 | Freier |
| 2002/0072861 A1 | 6/2002 | Ramakrishnan et al. |

FOREIGN PATENT DOCUMENTS

| | | |
|---|---|---|
| WO | WO 0056746 | 9/2000 |
| WO | WO 0075372 | 12/2000 |
| WO | WO 0114398 | 3/2001 |

OTHER PUBLICATIONS

Wanli Lu., http://ir.library.oregonstate.edu/xmlui/bitstream/handle/1957/28074/LuWanli2012.pdf?sequence=1, Feb. 23, 2012.*
Brodersen et al. "The Structural Basis for the Action of the Antibiotics Tetracycline, Pactamycin, and Hygromycin B on the 30S Ribosomal Subunit." *Cell.* 103(2000):1143-1154.
Burman et al. "Analysis of rRNA Processing and Translation in Mammalian Cells Using a Synthetic 18S rRNA Expression System." *Nucleic Acids Res.* 40.16(2012):8085-8098.
Dinos et al. "Dissecting the Ribosomal Inhibition Mechanisms of Edeine and Pactamycin: The Universally Conserved Residues G693 and C795 Regulate P-Site RNA Binding." *Mol. Cell.* 13.1(2004):113-124.
Dresios et al. "An mRNA-rRNA Base-Pairing Mechanism for Translation Initiation in Eukaryotes." *Nat. Struct. Mol. Biol.* 13.1(2006):30-34.
Hui et al. "Specialized Ribosome System: Preferential Translation of a Single mRNA Species by a Subpopulation of Mutated Ribosomes in *Escherichia coli.*" *PNAS.* 84.14(1987):4762-4766.
Mankin. "Pactamycin Resistance Mutations in Functional Sites of 16 S rRNA." *J. Mol. Biol.* 274.1(1997):8-15.
Agafonov et al., "Ribosome-associated protein that inhibits translation at the aminoacyl-tRNA binding stage," *EMBO Rep.* 2(5): 399-402 (2001).
Andersen and Leevers, "The essential *Drosophila* ATP-binding cassette domain protein, pixie, binds the 40 S ribosome in an ATP-dependent manner and is required for translation initiation," *J. Biol. Chem.* 282(20):14752-14760 (2007).
Arkin and Youvan, "An algorithm for protein engineering: simulations of recursive ensemble mutagenesis," *Proc. Natl. Acad. Sci. USA* 89(16):7811-7815 (1992).
Arnold, "Protein engineering for unusual environments," *Curr. Opinion Biotechnol.* 4(4):450-455 (1993).
Ashraf et al., "Single atom modification (O→S) of tRNA confers ribosome binding," *RNA* 5(2):188-194 (1999).
Bartel and Szostak, "Isolation of new ribozymes from a large pool of random sequences," *Science* 261(5127):1411-1418 (1993).
Botstein et al. "Making mutations in vitro and putting them back into yeast," Miami Wntr. Symp. vol. 19, 1982, pp. 265-274.
Broach, "The yeast plasmid 2 mu circle," *Cell* 28(2):203-204 (1982).
Broach: "The Molecular Biology of the Yeast *Saccharomyces*: Life Cycle and Inheritance", Strathern, Jones and Broach (Eds), 1981, Cold Spring Harbor Laboratory, New York, pp. 445-470.

(Continued)

*Primary Examiner* — Cynthia B Wilder
(74) *Attorney, Agent, or Firm* — Cooley LLP; Ivor R. Elrifi; Christina K. Stock

(57) ABSTRACT

Provided herein is a synthetic or isolated polynucleotide encoding a mammalian 18S rRNA that is resistant to pactamycin. The pactamycin-resistance is conferred by one or more single residue substitutions in the 18S rRNA sequence; a fragment thereof harboring said substitutions; a complementary sequence thereto; or a substantially identical sequence of the foregoing. Related systems, methods and kits are also described.

23 Claims, 9 Drawing Sheets

(56) References Cited

OTHER PUBLICATIONS

Brunelle et al, "Peptide release on the ribosome depends critically on the 2' OH of the peptidyl-tRNA substrate," *RNA* 14(8):1526-1531 (2008).
Burakovsky et al. "Mutations at the accommodation gate of the ribosome impair RF2-dependent translation termination," *RNA* 16(9):1848-1853 (2010).
Chadwick et al, "Safety of a single aerosol administration of escalating doses of the cationic lipid GL-67/DOPE/DMPE-PEG5000 formulation to the lungs of normal volunteers," *Gene Therapy* 4(9):937-942 (1997).
Champney, "Three methods to assay inhibitors of ribosomal subunitassembly," *Methods Mol. Med.* 142:63-73 (2008).
Day and Janssen, "Isolation and characterization of ribosomes and translation initiation factors from the gram-positive soil bacterium *Streptomyces lividans*," *J. Bacteriol.* 186(20):6864-6875 (2004).
Delagrave and Youvan, "Searching sequence space to engineer proteins: exponential ensemble mutagenesis," *Biotechnol. Res.* 11(13):1548-1552 (1993).
Bollon and Stauver, "DNA Transformation Efficiency of Various Bacterial and Yeast Host-Vector Systems", *Journal of Clinical Hematology and Oncology*, vol. 10, No. 2 & 3, pp. 39-48, (1980).
Gao and Huang, "Cationic liposome-mediated gene transfer," *Gene Therapy* 2(10):710-722 (1995).
Genbank Accession No. JQ247698, 2 Pages.
Genbank Accession No. NR003278, 3 pages.
Genbank Accession No. X00686, 2 pages.
Genbank Accession No. X00686.1, 2 pages.
Genbank Accession No. X82564, 7 pages.
Genbank Accession No. K03432, 2 pages.
Genbank Accession No. M10098, 2 pages.
Genbank Accession No. M11188, 2 pages.
Genbank Accession No. X01117. 2 pages.
Genbank Accession No. X03205, 4 pages.
Genbank Accesstion No. X06778, 2 pages.
Goddard et al., "A second dose of a CFTR cDNA-liposome complex is as effective as the first dose in restoring cAMP-dependent chloride secretion to null CF mice trachea," *Gene Ther.* 4(11):1231-1236 (1997).
Gokhale et al., "Antisense raf oligodeoxyribonucleotide is protected by liposomal encapsulation and inhibits Raf-1 protein expression in vitro and in vivo: implication for gene therapy of radioresistant cancer" *Gene Ther.* 4(12):1289-1299 (1997).
Gong et al., "Ribosome recycling factor and release factor 3 action promotes TnaC-peptidyl-tRNA Dropoff and relieves ribosome stalling during tryptophan induction of tna operon expression in *Escherichia coli*," J Bacteriol. 189(8):3147-3155 (2007).
Gorman et al., "Efficient in vivo delivery of DNA to pulmonary cells using the novel lipid EDMPC," *Gene Ther.* 4(9):983-992 (1997).
Henikoff and Henikoff, "Amino acid substitution matrices from protein blocks," *Proc. Natl. Acad. Sci. USA* 89(22):10915-10919 (1989).
Jasny, "Insect viruses invade biotechnology," *Science* 238(4834):1653 (1987).
Kalies et al., "Binding of ribosomes to the rough endoplasmic reticulum mediated by the Sec61p-complex," *J. Cell Biol.* 126(4):925-934 (1994).

Khan et al.,"Effects of poly(A)-binding protein on the interactions of translation initiation factor eIF4F and el F4F.4B with internal ribosome entry site (IRES) of tobacco etch virus RNA," *Biochim. Biophys. Acta* 1779(10):622-627 (2008).
Klostermeier et al.,"A three-fluorophore FRET assay for high-throughput screening of small-molecule inhibitors of ribosome assembly," *Nucleic Acids Res.* 32(9):2707-2715 (2004).
Lill and Wintermeyer, "Quantitative indicator assay of tRNA binding to the ribosomal P and A sites," *Methods Enzymol.* 164:597-611 (1988).
McCallum and Maden, "Human 18 S ribosomal RNA sequence inferred from DNA sequence. Variations in 18 S sequences and secondary modification patterns between vertebrates," *Biochem. J.* 232(3):725-733 (1985).
Merrill and Gromeier, "The double-stranded RNA binding protein 76:NF45 heterodimer inhibits translation initiation at the rhinovirus type 2 internal ribosome entry site," *J. Virol.* 80(14):6936-6942 (2006).
Monahan et al. "Direct intramuscular injection with recombinant AAV vectors results in sustained expression in a dog model of hemophilia," *Gene Ther*. 5(1):40-49 (1998).
Onodera et al. "Successful peripheral T-lymphocyte-directed gene transfer for a patient with severe combined immune deficiency caused by adenosine deaminase deficiency," *Blood* vol. 91, 1998, pp. 30-36.
Pestov et al., "Assays for ribosomal RNA processing and ribosome assembly" *Curr. Protoc. Cell Biol.*, 2008, Chapter 22:Unit 22.11.
Prinz et al., "Evolutionarily conserved binding of ribosomes to the translocation channel via the large ribosomal RNA," *EMBO J.* 19(8):1900-1906 (2000).
Rawat et al.,"Interactions of the release factor RF1 with the ribosome as revealed by cryo-EM," *J. Mol. Biol.* 357(4):1144-1153 (2006).
Raynal et al.,"Complete nucleotide sequence of mouse 18 S rRNA gene: comparison with other available homologs," *FEBS Lett.* 167(2):263-268 (1984).
Reidhaar-Olson and Sauer, "Combinatorial cassette mutagenesis as a probe of the informational content of protein sequences," *Science* 241(4861):53-57 (1988).
Rubin,"*Drosophila melanogaster* as an experimental organism," *Science* 240(4858):1453-1459 (1998).
Stemmer et al,"DNA shuffling by random fragmentation and reassembly: in vitro recombination for molecular evolution," *Proc. Natl. Acad. Sci. USA* 91(22):10747-10751 (1994).
Stemmer, "Rapid evolution of a protein in vitro by DNA shuffling," *Nature* 370(6488):389-391 (1994).
Sternberg et al.,"Translation factors direct intrinsic ribosome dynamics during translation termination and ribosome recycling," *Nat. Struct. Mol. Biol.* 16(8):861-868 (2009).
Sunohara et al.,"Ribosome stalling during translation elongation induces cleavage of mRNA being translated in *Escherichia coli*," *J. Biol Chem.* 279(15): 15368-15375 (2004).
Van Dyke et al.,"Stm1p alters the ribosome association of eukaryotic elongation factor 3 and affects translation elongation," *Nucleic Acids Res.* 37(18):6116-6125 (2009).
"Modification map for Human 18S rRNA (X03205)", Mar. 23, 2009 people.biochem.umass.edu/fournierlab/3dmodmap/hum18sseq.php (Jun. 21, 2010 version accessed via http://web.archive.org/web/20100621204948/http://people.biochem.umass.edu/fournierlab/3dmodmap/hum18sseq.php on Apr. 20, 2016).

* cited by examiner

SEQUENCE LISTING

```
<160> NUMBER OF SEQ ID NOS: 40

<210> SEQ ID NO 1
<211> LENGTH: 20
<212> TYPE: DNA
<213> ORGANISM: Mouse
<220> FEATURE:
<223> OTHER INFORMATION: rDNA.1

<400> SEQUENCE: 1
gacgttgcgc ctcgctgctg                                              20

<210> SEQ ID NO 2
<211> LENGTH: 20
<212> TYPE: DNA
<213> ORGANISM: Mouse
<220> FEATURE:
<223> OTHER INFORMATION: rDNA.2
```

-continued

<400> SEQUENCE: 2
cgcctcccgg cgaggacaca                                               20

<210> SEQ ID NO 3
<211> LENGTH: 27
<212> TYPE: DNA
<213> ORGANISM: Mouse
<220> FEATURE:
<221> NAME/KEY: misc_feature
<222> LOCATION: (1)..(3)
<223> OTHER INFORMATION: n is a, c, g, or t
      rDNA.3

<400> SEQUENCE: 3
nnnagatctg ggtcgaccag ttgttcc                                       27

<210> SEQ ID NO 4
<211> LENGTH: 20
<212> TYPE: DNA
<213> ORGANISM: Mouse
<220> FEATURE:
<223> OTHER INFORMATION: rDNA.4

<400> SEQUENCE: 4
caagtaggag aggagcgagc                                               20

<210> SEQ ID NO 5
<211> LENGTH: 20
<212> TYPE: DNA
<213> ORGANISM: Mouse
<220> FEATURE:
<223> OTHER INFORMATION: rDNA.5

<400> SEQUENCE: 5
ggtgtcttgc gcggtcttgg                                               20

<210> SEQ ID NO 6
<211> LENGTH: 20
<212> TYPE: DNA
<213> ORGANISM: Mouse
<220> FEATURE:
<223> OTHER INFORMATION: rDNA.6

<400> SEQUENCE: 6
cgctgagaag acggtcgaac                                               20

<210> SEQ ID NO 7
<211> LENGTH: 35
<212> TYPE: DNA
<213> ORGANISM: Mouse
<220> FEATURE:
<223> OTHER INFORMATION: rDNA.7

<400> SEQUENCE: 7
gatcgatgcg gccgcgtatc ggtatttcgg gtgtg                              35

<210> SEQ ID NO 8
<211> LENGTH: 14
<212> TYPE: DNA
<213> ORGANISM: Mouse
<220> FEATURE:
<223> OTHER INFORMATION: rDNA.8

<400> SEQUENCE: 8
caagcttctg cagg                                                     14

```
<210> SEQ ID NO 9
<211> LENGTH: 22
<212> TYPE: DNA
<213> ORGANISM: Mouse
<220> FEATURE:
<223> OTHER INFORMATION: rDNA.9

<400> SEQUENCE: 9
ctagcctgca gaagcttgag ct                                              22

<210> SEQ ID NO 10
<211> LENGTH: 44
<212> TYPE: DNA
<213> ORGANISM: Mouse
<220> FEATURE:
<223> OTHER INFORMATION: rDNA.10

<400> SEQUENCE: 10
taatacgact cactataggg tacctggttg atcctgccag tagc                      44

<210> SEQ ID NO 11
<211> LENGTH: 24
<212> TYPE: DNA
<213> ORGANISM: Mouse
<220> FEATURE:
<223> OTHER INFORMATION: rDNA.11

<400> SEQUENCE: 11
taatgatcct tccgcaggtt cacc                                            24

<210> SEQ ID NO 12
<211> LENGTH: 32
<212> TYPE: DNA
<213> ORGANISM: Mouse
<220> FEATURE:
<221> NAME/KEY: misc_feature
<222> LOCATION: (1)..(3)
<223> OTHER INFORMATION: n is a, c, g, or t
      rDNA.12

<400> SEQUENCE: 12
nnngctagcg tactgacacg ctgtcctttc cc                                   32

<210> SEQ ID NO 13
<211> LENGTH: 24
<212> TYPE: DNA
<213> ORGANISM: Mouse
<220> FEATURE:
<223> OTHER INFORMATION: 24-nthybridization tag

<400> SEQUENCE: 13
aggcccatct ctgctaggag agct                                            24

<210> SEQ ID NO 14
<211> LENGTH: 24
<212> TYPE: DNA
<213> ORGANISM: Mouse
<220> FEATURE:
<223> OTHER INFORMATION: a-tag probe

<400> SEQUENCE: 14
ctcctagcag agatgggcct agct                                            24

<210> SEQ ID NO 15
<211> LENGTH: 18
<212> TYPE: DNA
<213> ORGANISM: Mouse
```

```
<220> FEATURE:
<223> OTHER INFORMATION: a-5' ETS probe

<400> SEQUENCE: 15
gagagcgcga gagaggag                                                 18

<210> SEQ ID NO 16
<211> LENGTH: 18
<212> TYPE: DNA
<213> ORGANISM: Mouse
<220> FEATURE:
<223> OTHER INFORMATION: a-ITS1 probe

<400> SEQUENCE: 16
acacacaaga cggggaga                                                 18

<210> SEQ ID NO 17
<211> LENGTH: 17
<212> TYPE: DNA
<213> ORGANISM: Mouse
<220> FEATURE:
<223> OTHER INFORMATION: a-18S rRNA probe

<400> SEQUENCE: 17
gccccgcggg acactca                                                  17

<210> SEQ ID NO 18
<211> LENGTH: 20
<212> TYPE: DNA
<213> ORGANISM: Mouse
<220> FEATURE:
<223> OTHER INFORMATION: 693RT

<400> SEQUENCE: 18
gtcttgcgcc ggtccaagaa                                               20

<210> SEQ ID NO 19
<211> LENGTH: 27
<212> TYPE: DNA
<213> ORGANISM: Mouse
<220> FEATURE:
<221> NAME/KEY: misc_feature
<222> LOCATION: (1)..(3)
<223> OTHER INFORMATION: n is a, c, g, or t
      Pol-I.1

<400> SEQUENCE: 19
nnnagatctg ggtcgaccag ttgttcc                                       27

<210> SEQ ID NO 20
<211> LENGTH: 32
<212> TYPE: DNA
<213> ORGANISM: Mouse
<220> FEATURE:
<221> NAME/KEY: misc_feature
<222> LOCATION: (1)..(3)
<223> OTHER INFORMATION: n is a, c, g, or t
      Pol-I.2

<400> SEQUENCE: 20
nnngctagct acctatctcc aggtccaata gg                                 32

<210> SEQ ID NO 21
<211> LENGTH: 29
<212> TYPE: DNA
<213> ORGANISM: Mouse
```

```
<220> FEATURE:
<221> NAME/KEY: misc_feature
<222> LOCATION: (1)..(3)
<223> OTHER INFORMATION: n is a, c, g, or t
      Pol-I.3

<400> SEQUENCE: 21
nnngcggccg cgtgggatcc ccatcctcg                                             29

<210> SEQ ID NO 22
<211> LENGTH: 29
<212> TYPE: DNA
<213> ORGANISM: Mouse
<220> FEATURE:
<221> NAME/KEY: misc_feature
<222> LOCATION: (1)..(3)
<223> OTHER INFORMATION: n is a, c, g, or t
      Pol-I.4

<400> SEQUENCE: 22
nnncaattgc gaccaccaga ctttctgac                                             29

<210> SEQ ID NO 23
<211> LENGTH: 1871
<212> TYPE: DNA
<213> ORGANISM: Mouse
<220> FEATURE:
<223> OTHER INFORMATION: Mouse Gene for 18S rRNA
<308> DATABASE ACCESSION NUMBER: GenBank No. JQ247698
<309> DATABASE ENTRY DATE: 2012-12-07

<400> SEQUENCE: 23
tacctggttg atcctgccag tagcatatgc ttgtctcaaa gattaagcca tgcatgtcta            60
agtacgcacg gccggtacag tgaaactgcg aatggctcat taaatcagtt atggttcctt          120
tggtcgctcg ctcctctcct acttggataa ctgtggtaat tctagagcta atacatgccg          180
acgggcgctg accccccttc ccggggggg atgcgtgcat ttatcagatc aaaaccaacc           240
cggtgagctc cctcccggct ccggccgggg gtcgggcgcc ggcggctttg gtgactctag          300
ataacctcgg gccgatcgca cgccccccgt ggcggcgacg acccattcga acgtctgccc          360
tatcaacttt cgatggtagt cgccgtgcct accatggtga ccacgggtga cggggaatca          420
gggttcgatt ccggagaggg agcctgagaa acggctacca catccaagga aggcagcagg          480
cgcgcaaatt acccactccc gacccgggga ggtagtgacg aaaaataaca atacaggact          540 cttttcgaggc cctgtaattg gaatgagtcc actttaaatc ctttaacgag gatccattgg          600
agggcaagtc tggtgccagc agccgcggta attccagctc caatagcgta tattaaagtt          660
gctgcagtta aaaagctcgt agttggatct gggagcggg cggcggtcc gccgcgaggc           720 gagtcaccgc ccgtccccgc cccttgcctc tcggcgcccc ctcgatgctc ttagctgagt          780
gtcccgcggg gcccgaagcg tttactttga aaaaattaga gtgttcaaag caggcccgag          840
ccgcctggat accgcagcta ggaataatgg aataggaccg cggttctatt tgttggtttt          900
tcggaactga ggccatgatt aagagggacg gccgggggca ttcgtattgc gccgctagag          960
gtgaaattct tggaccggcg caagacggac cagagcgaaa gcatttgcca agaatgtttt         1020
cattaatcaa gaacgaaagt cggaggttcg aagacgatca gataccgtcg tagttccgac         1080
cataaacgat gccgactggc gatgcggcgg cgttattccc atgacccgcc gggcagcttc         1140
cgggaaacca agtctttggg ttccggggg gagtatggtt gcaaagctga aacttaaagg          1200
aattgacgga agggcaccac caggagtgga gcctgcggct taatttgact caacacggga         1260
```

-continued

| | |
|---|---|
| aacctcacccc ggcccggaca cggacaggat tgacagattg atagctctt ctcgattccg | 1320 |
| tgggtggtgg tgcatggccg ttcttagttg gtggagcgat ttgtctggtt aattccgata | 1380 |
| acgaacgaga ctctggcatg ctaactagtt acgcgacccc cgagcggtcg gcgtccccca | 1440 |
| acttcttaga gggacaagtg gcgttcagcc acccgagatt gagcaataac aggtctgtga | 1500 |
| tgcccttaga tgtccggggc tgcacgcgcg ctacactgac tggctcagcg tgtgcctacc | 1560 |
| ctacgccggc aggcgcgggt aacccgttga accccattcg tgatggggat cggggattgc | 1620 |
| aattattccc catgaacgag gaattcccag taagtgcggg tcataagctt gcgttgatta | 1680 |
| agtccctgcc ctttgtacac accgcccgtc gctactaccg attggatggt ttagtgaggc | 1740 |
| cctcggatcg gccccgccgg ggtcggccca cggccctggc ggagcgctga aagacggtc | 1800 |
| gaacttgact atctagagga agtaaaagtc gtaacaaggt ttccgtaggt gaacctgcgg | 1860 |
| aaggatcatt a | 1871 |

<210> SEQ ID NO 24
<211> LENGTH: 1869
<212> TYPE: DNA
<213> ORGANISM: Human
<220> FEATURE:
<223> OTHER INFORMATION: Human Gene for 18S rRNA
<308> DATABASE ACCESSION NUMBER: GenBank No. X03205
<309> DATABASE ENTRY DATE: 1994-12-16

<400> SEQUENCE: 24

| | |
|---|---|
| tacctggttg atcctgccag tagcatatgc ttgtctcaaa gattaagcca tgcatgtcta | 60 |
| agtacgcacg gccggtacag tgaaactgcg aatggctcat taaatcagtt atggttcctt | 120 |
| tggtcgctcg ctcctctccc acttggataa ctgtggtaat tctagagcta atacatgccg | 180 |
| acgggcgctg acccccttcg cggggggggat gcgtgcattt atcagatcaa aaccaacccg | 240 |
| gtcagcccct ctccggcccc ggccggggggg cgggcgccgg cggctttggt gactctagat | 300 |
| aacctcgggc cgatcgcacg cccccgtgg cggcgacgac ccattcgaac gtctgcccta | 360 |
| tcaactttcg atggtagtcg ccgtgcctac catggtgacc acgggtgacg gggaatcagg | 420 |
| gttcgattcc ggagagggag cctgagaaac ggctaccaca tccaaggaag gcagcaggcg | 480 |
| cgcaaattac ccactcccga cccggggagg tagtgacgaa aaataacaat acaggactct | 540 |
| ttcgaggccc tgtaattgga atgagtccac tttaaatcct ttaacgagga tccattggag | 600 |
| ggcaagtctg gtgccagcag ccgcggtaat tccagctcca atagcgtata ttaaagttgc | 660 |
| tgcagttaaa aagctcgtag ttggatcttg ggagcgggcg gcggtccgc cgcgaggcga | 720 |
| gccaccgccc gtccccgccc cttgcctctc ggcgcccct cgatgctctt agctgagtgt | 780 |
| cccgcggggc ccgaagcgtt tactttgaaa aaattagagt gttcaaagca ggcccgagcc | 840 |
| gcctggatac cgcagctagg aataatggaa taggaccgcg gttctatttt gttggttttc | 900 |
| ggaactgagg ccatgattaa gagggacggc cgggggcatt cgtattgcgc cgctagaggt | 960 |
| gaaattcttg gaccggcgca agacggacca gagcgaaagc atttgccaag aatgttttca | 1020 |
| ttaatcaaga acgaaagtcg gaggttcgaa gacgatcaga taccgtcgta gttccgacca | 1080 |
| taaacgatgc cgaccggcga tgcggcggcg ttattcccat gacccgccgg gcagcttccg | 1140 |
| ggaaaccaaa gtctttgggt tccggggggga gtatggttgc aaagctgaaa cttaaaggaa | 1200 |
| ttgacggaag ggcaccacca ggagtggagc ctgcggctta atttgactca acacgggaaa | 1260 |
| cctcacccgg cccggacacg gacaggattg acagattgat agctctttct cgattccgtg | 1320 |
| ggtggtggtg catggccgtt cttagttggt ggagcgattt gtctggttaa ttccgataac | 1380 |

-continued

```
gaacgagact ctggcatgct aactagttac gcgaccccg agcggtcggc gtcccccaac    1440
ttcttagagg acaagtggc gttcagccac ccgagattga gcaataacag gtctgtgatg    1500
cccttagatg tccggggctg cacgcgcgct acactgactg gctcagcgtg tgcctaccct    1560
acgccggcag gcgcgggtaa cccgttgaac cccattcgtg atggggatcg gggattgcaa    1620
ttattcccca tgaacgagga attcccagta agtgcgggtc ataagcttgc gttgattaag    1680
tccctgccct tgtacacac cgcccgtcgc tactaccgat tggatggttt agtgaggccc    1740
tcggatcggc cccgccgggg tcggcccacg gccctggcgg agcgctgaga agacggtcga    1800
acttgactat ctagaggaag taaaagtcgt aacaaggttt ccgtaggtga acctgcggaa    1860
ggatcatta                                                            1869

<210> SEQ ID NO 25
<211> LENGTH: 15
<212> TYPE: DNA
<213> ORGANISM: Mouse
<220> FEATURE:
<223> OTHER INFORMATION: U3 snoRNA 5' hinge region

<400> SEQUENCE: 25
ttactagaga agttt                                                     15

<210> SEQ ID NO 26
<211> LENGTH: 15
<212> TYPE: DNA
<213> ORGANISM: Mouse
<220> FEATURE:
<223> OTHER INFORMATION: p18S.1

<400> SEQUENCE: 26
atcgatctct tcctt                                                     15

<210> SEQ ID NO 27
<211> LENGTH: 9
<212> TYPE: DNA
<213> ORGANISM: Mouse
<220> FEATURE:
<223> OTHER INFORMATION: p18S.8delta

<400> SEQUENCE: 27 atcgacctt                                                             9

<210> SEQ ID NO 28
<211> LENGTH: 15
<212> TYPE: DNA
<213> ORGANISM: Mouse
<220> FEATURE:
<223> OTHER INFORMATION: p18S.8m

<400> SEQUENCE: 28
atcgaagaga acctt                                                     15

<210> SEQ ID NO 29
<211> LENGTH: 31
<212> TYPE: DNA
<213> ORGANISM: Mouse
<220> FEATURE:
<223> OTHER INFORMATION: Partial sequence of wildtype 18S rRNA

<400> SEQUENCE: 29
tagaggtgaa attcttggac cttcttaaga c                                   31
```

```
<210> SEQ ID NO 30
<211> LENGTH: 31
<212> TYPE: DNA
<213> ORGANISM: Mouse
<220> FEATURE:
<223> OTHER INFORMATION: mouse 18S rRNA

<400> SEQUENCE: 30
tagaggtaaa attcttggac cttcttaaga c                             31

<210> SEQ ID NO 31
<211> LENGTH: 20
<212> TYPE: DNA
<213> ORGANISM: Mouse
<220> FEATURE:
<223> OTHER INFORMATION: oligonucleotide primer 693RT

<400> SEQUENCE: 31
aagaacctgg ccgcgttctg                                          20

<210> SEQ ID NO 32
<211> LENGTH: 24
<212> TYPE: DNA
<213> ORGANISM: Mouse
<220> FEATURE:
<223> OTHER INFORMATION: 4-nt-extended products from wild-type 18S rRNA
      templates

<400> SEQUENCE: 32
ctttaagaac ctggccgcgt tctg                                     24

<210> SEQ ID NO 33
<211> LENGTH: 26
<212> TYPE: DNA
<213> ORGANISM: Mouse
<220> FEATURE:
<223> OTHER INFORMATION: 6-nt-extended products from G693A-mutated 18S
      rRNA

<400> SEQUENCE: 33
cattttaaga acctggccgc gttctg                                   26

<210> SEQ ID NO 34
<211> LENGTH: 1869
<212> TYPE: DNA
<213> ORGANISM: Mouse
<220> FEATURE:
<223> OTHER INFORMATION: mouse 18S rDNA sequence
<308> DATABASE ACCESSION NUMBER: GenBank No. X00686
<309> DATABASE ENTRY DATE: 1991-04-10

<400> SEQUENCE: 34
tacctggttg atcctgccag tagcatatgc ttgtctcaaa gattaagcca tgcatgtcta      60
agtacgcacg gccggtacag tgaaactgcg aatggctcat taaatcagtt atggttcctt    120
tggtcgctcg ctcctctcct acttggataa ctgtggtaat tctagagcta atacatgccg    180
acgggcgctg accccccttc ccgggggggg atgcgtgcat ttatcagatc aaaaccaacc    240
cggtgagctc cctcccggct ccggccgggg gtcgggcgcc ggcggcttgg tgactctaga    300
taacctcggg ccgatcgcac gccccccgtg gcggcgacga cccattcgaa cgtctgccct    360
atcaactttc gatggtagtc gccgtgccta ccatggtgac cacgggtgac ggggaatcag    420
ggttcgattc cggagaggga gcctgagaaa cggctaccac atccaaggaa ggcagcaggc    480
gcgcaaatta cccactcccg acccggggag gtagtgacga aaaataacaa tacaggactc    540
```

-continued

```
tttcgaggcc ctgtaattgg aatgagtcca ctttaaatcc tttaacgagg atccattgga    600
gggcaagtct ggtgccagca gccgcggtaa ttccagctcc aatagcgtat attaaagttg    660
ctgcagttaa aaagctcgta gttggatctt gggagcgggc gggcggtccg ccgcgaggcg    720
agtcaccgcc cgtccccgcc ccttgcctct cggcgccccc tcgatgctct tagctgagtg    780
tcccgcgggg cccgaagcgt ttactttgaa aaaattagag tgttcaaagc aggcccgagc    840
cgcctggata ccgcagctag gaataatgga ataggaccgc ggttctattt tgttggtttt    900
cggaactgag gccatgatta agagggacgg ccgggggcat tcgtattgcg ccgctagagg    960
tgaaattctt ggaccggcgc aagacggacc agagcgaaag catttgccaa gaatgttttc   1020
attaatcaag aacgaaagtc ggaggttcga agacgatcag ataccgtcgt agttccgacc   1080
ataaacgatg ccgactggcg atgcggcggc gttattccca tgacccgccg ggcagcttcc   1140
gggaaaccaa agtctttggg ttccgggggg agtatggttg caaagctgaa acttaaagga   1200
attgacggaa gggcaccacc aggagtgggc ctgcggctta atttgactca acacgggaaa   1260
cctcacccgg cccggacacg gacaggattg acagattgat agctctttct cgattccgtg   1320
ggtggtggtg catggccgtt cttagttggt ggagcgattt gtctggttaa ttccgataac   1380
gaacgagact ctggcatgct aactagttac gcgacccccg agcggtcggc gtcccccaac   1440
ttcttagagg gacaagtggc gttcagccac ccgagattga gcaataacag gtctgtgatg   1500
cccttagatg tccggggctg cacgcgcgct acactgactg gctcagcgtg tgcctaccct   1560
gcgccggcag gcgcgggtaa cccgttgaac cccattcgtg atggggatcg gggattgcaa   1620
ttattcccca tgaacgagga attcccagta agtgcgggtc ataagcttgc gttgattaag   1680
tccctgccct ttgtacacac cgcccgtcgc tactaccgat tggatggttt agtgaggccc   1740
tcggatcggc cccgccgggg tcggcccacg gccctggcgg agcgctgaga agacggtcga   1800
acttgactat ctagaggaag taaaagtcgt aacaaggttt ccgtaggtga acctgcggaa   1860
ggatcatta                                                           1869

<210> SEQ ID NO 35
<211> LENGTH: 1870
<212> TYPE: DNA
<213> ORGANISM: Mouse
<220> FEATURE:
<223> OTHER INFORMATION: mouse 18S rRNA sequence
<308> DATABASE ACCESSION NUMBER: GenBank No. NR_003278
<309> DATABASE ENTRY DATE: 2013-04-20

<400> SEQUENCE: 35
acctggttga tcctgccagg tagcatatgc ttgtctcaaa gattaagcca tgcatgtcta     60
agtacgcacg gccggtacag tgaaactgcg aatggctcat taaatcagtt atggttcctt    120
tggtcgctcg ctcctctcct acttggataa ctgtggtaat tctagagcta atacatgccg    180
acgggcgctg acccccttc ccggggggggg atgcgtgcat ttatcagatc aaaaccaacc    240
cggtgagctc cctcccggct ccggccgggg gtcgggcgcc ggcggcttgg tgactctaga    300
taacctcggg ccgatcgcac gccccccgtg gcggcgacga cccattcgaa cgtctgccct    360
atcaactttc gatggtagtc gccgtgccta ccatggtgac cacgggtgac ggggaatcag    420
ggttcgattc cggagaggga gcctgagaaa cggctaccac atccaaggaa ggcagcaggc    480
gcgcaaatta cccactcccg acccggggag gtagtgacga aaaataacaa tacaggactc    540
tttcgaggcc ctgtaattgg aatgagtcca ctttaaatcc tttaacgagg atccattgga    600
gggcaagtct ggtgccagca gccgcggtaa ttccagctcc aatagcgtat attaaagttg    660
```

```
ctgcagttaa aaagctcgta gttggatctt gggagcgggc gggcggtccg ccgcgaggcg    720
agtcaccgcc cgtccccgcc ccttgcctct cggcgccccc tcgatgctct tagctgagtg    780
tcccgcgggg cccgaagcgt ttactttgaa aaaattagag tgttcaaagc aggcccgagc    840
cgcctggata ccgcagctag gaataatgga ataggaccgc ggttctattt tgttggtttt    900
cggaactgag gccatgatta agagggacgg ccgggggcat tcgtattgcg ccgctagagg    960
tgaaattctt ggaccggcgc aagacggacc agagcgaaag catttgccaa gaatgttttc   1020
attaatcaag aacgaaagtc ggaggttcga agacgatcag ataccgtcgt agttccgacc   1080
ataaacgatg ccgactggcg atgcggcggc gttattccca tgacccgccg ggcagcttcc   1140
gggaaaccaa agtctttggg ttccgggggg agtatggttg caaagctgaa acttaaagga   1200
attgacggaa gggcaccacc aggagtgggc ctgcggctta atttgactca acacgggaaa   1260
cctcacccgg cccggacacg gacaggattg acagattgat agctctttct cgattccgtg   1320
ggtggtggtg catggccgtt cttagttggt ggagcgattt gtctggttaa ttccgataac   1380
gaacgagact ctggcatgct aactagttac gcgaccccccg agcggtcggc gtcccccaac   1440
ttcttagagg gacaagtggc gttcagccac ccgagattga gcaataacag gtctgtgatg   1500
cccttagatg tccggggctg cacgcgcgct acactgactg gctcagcgtg tgcctacccct   1560 gcgccggcag gcgcgggtaa cccgttgaac cccattcgtg atgggatcg gggattgcaa    1620 ttattcccca tgaacgagga attcccagta agtgcgggtc ataagcttgc gttgattaag    1680
tccctgccct ttgtacacac cgcccgtcgc tactaccgat tggatggttt agtgaggccc    1740
tcggatcggc cccgccgggg tcggcccacg gccctggcgg agcgctgaga agacggtcga    1800
acttgactat ctagaggaag taaaagtcgt aacaaggttt ccgtaggtga acctgcggaa    1860
ggatcattaa    1870

<210> SEQ ID NO 36
<211> LENGTH: 1874
<212> TYPE: DNA
<213> ORGANISM: Rat
<220> FEATURE:
<223> OTHER INFORMATION: Rat18S rDNA sequence
<308> DATABASE ACCESSION NUMBER: GenBank No. X01117
<309> DATABASE ENTRY DATE: 2003-06-06

<400> SEQUENCE: 36
tacctggttg atcctgccag tagcatatgc ttgtctcaaa gattaagcca tgcatgtcta     60
agtacgcacg gccggtacag tgaaactgcg aatggctcat taaatcagtt atggttcctt    120
tggtcgctcg ctcctctcct acttggataa ctgtggtaat tctagagcta atacatgccg    180
acgggcgctg accccccttc ccgtgggggg aacgcgtgca tttatcagat caaaaccaac    240
ccggtcagcc ccctcccggc tccggccggg ggtcgggcgc cggcggcttt ggtgactcta    300 gataaccctcg ggccgatcgc acgtcccccgt ggcggcgacg acccattcga acgtctgccc    360
tatcaacttt cgatggtagt cgccgtgcct accatggtga ccacgggtga cggggaatca    420
gggttcgatt ccggagaggg agcctgagaa acggctacca catccaagga aggcagcagg    480
cgcgcaaatt acccactccc gacccgggga ggtagtgacg aaaaataaca atacaggact    540 cttttcgaggc cctgtaattg gaatgagtcc actttaaatc ctttaacgag gatccattgg    600
agggcaagtc tggtgccagc agccgcggta attccagctc caatagcgta tattaaagtt    660
gctgcagtta aaagctcgt agttggatct tgggagcggg cggcggtcc gccgcgaggc     720 gagctcaccg cccgtgtcccc agcccctgcc tctcggcgcc ccctcgatgc tcttagctga    780
```

```
gtgtcccgcg gggcccgaag cgtttacttt gaaaaaatta gagtgttcaa agcaggcccg    840
agccgcctgg ataccgcagc taggaataat ggaataggac cgcggttcta ttttgttggt    900
tttcggaact gaggccatga ttaagaggga cggccggggg cattcgtatt gcgccgctag    960
aggtgaaatt cttggaccgg cgcaagacga accagagcga aagcatttgc caagaatgtt   1020
ttcattaatc aagaacgaaa gtcggaggtt cgaagacgat cagataccgt cgtagttccg   1080
accataaacg atgccgactg gcgatgcggc ggcgttattc ccatgacccg ccgggcagct   1140
tccgggaaac caaagtcttt gggttccggg ggagtatgg ttgcaaagct gaaacttaaa   1200
ggaattgacg aagggcacc accaggagtg gagcctgcgg cttaatttga ctcaacacgg   1260
gaaacctcac ccggcccgga cacggacagg attgacagat tgatagctct ttctcgattc   1320
cgtgggtggt ggtgcatggc cgttcttagt tggtggagcg atttgtctgg ttaattccga   1380
taacgaacga gactctcggc atgctaacta gttacgcgac ccccgagcgg tcggcgtccc   1440
ccaacttctt agagggacaa gtggcgttca gccaccgaga ttgagcaata acaggtctgt   1500
gatgccctta gatgtccggg gctgcacgcg cgctacactg aactggctca gcgtgtgcct   1560
accctacgcc ggcaggcgcg ggtaacccgt tgaacccat tcgtgatggg gatcggggat   1620
tgcaattatt ccccatgaac gaggaattcc cagtaagtgc gggtcataag cttgcgttga   1680
ttaagtccct gccctttgta cacaccgccc gtcgctacta ccgattggat ggtttagtga   1740
ggccctcgga tcggccccgc cggggtcggc ccacggcctt ggcggaggcc tgagaagacg   1800
gtcgaacttg actatctaga ggaagtaaaa gtcgtaacaa ggtttccgta ggtgaacctg   1860
cggaaggatc atta                                                     1874
```

<210> SEQ ID NO 37
<211> LENGTH: 1920
<212> TYPE: DNA
<213> ORGANISM: rat
<220> FEATURE:
<223> OTHER INFORMATION: mouse 18S rDNA sequence
<308> DATABASE ACCESSION NUMBER: GenBank No. M11188
<309> DATABASE ENTRY DATE: 1993-04-27

<400> SEQUENCE: 37

```
tcgcgctcct tacctggttg atcctgccag tagcatatgc ttgtctcaaa gattaagcca     60
tgcatgtcta agtacgcacg gccggtacag tgaaactgcg aatggctcat taaatcagtt    120
atggttcctt tgtcgctcgc tcctctccta cttggataac tgtggtaatt ctagagctaa    180
tacatgccga cggcgctga ccccccttcc cgtgggggg acgcgtgcat ttatcagatc    240
aaaaccaacc cggtcagccc cctcccggct ccggccgggg gtcgggcgcc ggacggcttt    300
ggtgactcta gataaccctcg gccgatcgc acgccctccg tggcggcgac gacccattcg    360
aacgtctgcc ctatcaactt cgatggtag tcgccgtgcc taccatggtg accacgggtg    420
acggggaatc agggttcgat tccggagagg gagcctgaga acggctacc acatccaagg    480 aaggcagcag gcgcgcaaat tacccactcc cgacccgggg aggtagtgac gaaaaataac    540
aatacaggac tctttcgagg ccctgtaatt ggaatgagtc cactttaaat cctttaacga    600
ggatccattg gagggcaagt ctggtgccag cagccgcggt aattccagct ccaatagcgt    660
atattaaagt tgctgcagtt aaaaagctcg tagttggatc ttgggagcgg gcgggcggtc    720
cgccgcgagg cgagtcaccg cccgtccccg cccttgcct ctcggcgccc ctcgatgct    780 cttagctgag tgtcccgcgg ggcccgaagc gtttactttg aaaaattag agtgttcaaa    840 gcaggcccga gccgcctaga taccgcagct aggaataatg gaataggacc gcggttctat    900
```

| | |
|---|---:|
| tttgttggtt ttcggaactg aggccatgat taagagggac ggccgggggc attcgtattg | 960 |
| cgccgctaga ggtgaaattc ttggaccggc gcaagacgga ccagagcgaa agcatttgcc | 1020 |
| aagaatgttt tcattaatca agaacgaaag tcggaggttc gaagacgatc agataccgtc | 1080 |
| gtagttccga ccataaacga tgccgactgg cgatgcggcg gcgttattcc catgacccgc | 1140 |
| cgggcagctt ccgggaaacc aaagtctttg ggttccgggg ggagtatggt tgcaaagctg | 1200 |
| aaacttaaag gaattgacgg aagggcacca ccaggagtgg gcctgcggct taatttgact | 1260 |
| caacacggga aacctcaccc ggcccggaca cggacaggat tgacagattg atagctcttt | 1320 |
| ctcgattccg tgggtggtgg tgcatggccg ttcttagttg gtggagcgat ttgtctggtt | 1380 |
| aattccgata acgaacgaga ctctggcatg ctaactagtt acgcgacccc cgagcggtcg | 1440 |
| gcgtccccca acttcttaga gggacaagtg gcgttcagcc acccgagatt gagcaataac | 1500 |
| aggtctgtga tgcccttaga tgtccggggc tgcacgcgcg ctacactgac tggctcagcg | 1560 |
| tgtgcctacc ctacgccggc aggcgcgggt aacccgttga accccattcg tgatggggat | 1620 |
| cggggattgc aattattccc catgaacgag gaattcccag taagtgcggg tcataagctt | 1680 |
| gcgttgatta agtccctgcc cttttgtacac accgcccgtc gctactaccg attggatggt | 1740 |
| ttagtgaggc cctcggatcg gccccgccgg ggtcggccca cggccttgcg gagcgctgag | 1800 |
| aagacggtcg aacttgacta tctagaggaa gtaaaagtcg taacaaggtt tccgtaggtg | 1860 |
| aacctgcgga aggatcatta acggagaagg ccgagggggg tcgtcgtccc gtccctcttg | 1920 |

<210> SEQ ID NO 38
<211> LENGTH: 1863
<212> TYPE: DNA
<213> ORGANISM: Rabbit
<220> FEATURE:
<223> OTHER INFORMATION: Rabbit18S rDNA sequence
<308> DATABASE ACCESSION NUMBER: GenBank No. X06778
<309> DATABASE ENTRY DATE: 2003-06-06

<400> SEQUENCE: 38

| | |
|---|---:|
| tacctggttg atcctgccag tagcatatgc ttgtctcaaa gattaagcca tgcatgtcta | 60 |
| agtacgcacg gccggtacag tgaaactgcg aatggctcat taaatcagtt atggttcctt | 120 |
| tggtcgctcg ctcctctcct acttggataa ctgtggtaat tctagagcta atacatgccg | 180 |
| acggcgctga ctccctttgt gtgggatgcg tgcatttatc agatcaaaac caacccggtc | 240 |
| agcctccccg ccggccgggg gggtggggcg gcggctttgg tgactctaga taacctcggg | 300 |
| ccgatcgcag ccctccgtgg cggcgacgac ccattcgaac gtctgcccta tcaactttcg | 360 |
| atggtagtcg ccgtgcctac catggtgacc acgggtgacg gggaatcagg gttcgattcc | 420 |
| ggagagggag cctgagaaac ggctaccaca tccaaggaag gcagcaggcg cgcaaattac | 480 |
| ccactcccga cccggggagg tagtgacgaa aaataacaat acaggactct tcgaggccc | 540 |
| tgtaattgga atgagtccac tttaaatcct ttaacgagga tccattggag ggcaagtctg | 600 |
| gtcgcagcag ccgcggtaat tccagctcca atagcgtata ttaaagttgc tgcagttaaa | 660 |
| aagctcgtag ttggatcttg tggagggtgc gtagcgggcg gtccgccgcg aggcgagcca | 720 |
| ccgcccgtcc ccgccccttg cctctcggcg cccctcgat gctcttagct gagtgtcccg | 780 |
| cggggcccga agcgtttact ttgaaaaaat tagagtgttc aaagcaggcc cgagccgcct | 840 |
| ggataccgca gctaggaata atggaatagg accgcggttc tattttgttg gtttccggaa | 900 |
| ctgaggccat gattaagagg gacggccggg gcattcgta ttgcgccgct agaggtgaaa | 960 |
| ttcttggacc ggcgcaagac ggaccagagc gaaagcattt gccaagaatg ttttcattaa | 1020 |

```
tcaagaacga aagtcggagg ttcgaagacg atcagatacc gtcgtagttc cgaccataaa    1080
cgatgccgac tggcgatgcg gcggcgttat tcccatgacc cgccgggcag cttccgggaa    1140
accaaagtct ttgggttccg gggggagtat ggttgcaaag ctgaaactta aaggaattga    1200
cggaagggca ccaccaggag tggagcctgc ggcttaattt gactcaacac gggaaacctc    1260
acccggcccg gacacggaca ggattgacag attgatagct ctttctcgat tctgtgggtg    1320
gtggtgcatg gccgttctta gttggtggag cgatttgtct ggttaattcc gataacgaac    1380
gagactctgg catgctaact agttacgcga ccccgagcg gtcggcgtcc cccaacttct    1440
tagagggaca gtggcgttc agccacccga gattgagcaa taacaggtct gtgatgccct    1500
tagatgtcgg ggctgcacgc gcgctacact gactggctca gcgtgtgcct accctacgcc    1560
ggcaggcgcg ggtaacccgt tgaacccat tcgtgatggg gatcgggat tgcaattatt    1620 ccccatgaac gaggaattcc cagtaagtgc gggtcataag cttgcgttga ttaagtccct    1680 gcccttttgta cacaccgccc gtcgctacta ccgattggat ggtttagtga ggccctcgga    1740
tcggcccgcc ggggtcggcc cacggccctg gcggagcgcg gagaagacgg tcgaacttga    1800
ctatctagag gaagtaaaag tcgtaacaag gtttccgtag gtgaacctgc ggaaggatca    1860
tta                                                                 1863

<210> SEQ ID NO 39
<211> LENGTH: 2235
<212> TYPE: DNA
<213> ORGANISM: Human
<220> FEATURE:
<221> NAME/KEY: misc_feature
<222> LOCATION: (61)..(64)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (97)..(101)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
      Human 18S rDNA sequence
<308> DATABASE ACCESSION NUMBER: GenBank No. K03432
<309> DATABASE ENTRY DATE: 1993-08-03

<400> SEQUENCE: 39
cgctgctcct cccgtcgccg tccgggcccg tccgtccgtc cgtccgtcgt cctcctcgct     60
nnnncggggc gccgggcccg tcctcacngg ccccgnnnn ngtccnggcc cgtcggggcc    120
tcgccgcgct ctaccttacc tacctggttg atcctgccag tagcatatgc ttgtctcaaa    180
gattaagcca tgcatgtcta agtacgcacg gccggtacag tgaaactgcg aatggctcat    240
taaatcagtt atggttcctt tggtcgctcg ctcctctcct acttggataa ctgtggtaat    300
tctagagcta atacatgccg acgggcgctg accccttcg cggggggat gcgtgcattt    360 atcgatcaa aaccaacccg gtcagcccct ctccggcccc ggccggggg cgggcgccgg    420 cggctttggt gactctagat aacctcgggc cgatcgcacg cccccgtgg cggcgacgac    480 ccattcgaac gtctgcccta tcaactttcg atggtagtcg ccgtgcctac catggtgacc    540
acgggtgacg gggaatcagg gttcgattcc ggagagggag cctgagaaac ggctaccaca    600
tccaaggaag gcagcaggcg cgcaaattac ccactcccga cccggggagg tagtgacgaa    660
```

| | |
|---|---|
| aaataacaat acaggactct ttcgaggccc tgtaattgga atgagtccac tttaaatcct | 720 |
| ttaacgagga tccattggag ggcaagtctg gtgccagcag ccgcggtaat tccagctcca | 780 |
| atagcgtata ttaaagttgc tgcagttaaa aagctcgtag ttggatcttg ggagcgggcg | 840 |
| ggcggtccgc cgcgaggcga gccaccgccc gtccccgccc cttgcctctc ggcgccccct | 900 |
| cgatgctctt agctgagtgt cccgcggggc ccgaagcgtt tactttgaaa aaattagagt | 960 |
| gttcaaagca ggcccgagcc gcctggatac cgcagctagg aataatggaa taggaccgcg | 1020 |
| gttctatttt gttggttttc ggaactgagg ccatgattaa gagggacggc cgggggcatt | 1080 |
| cgtattgcgc cgctagaggt gaaattcctt ggaccggcgc aagacggacc agagcgaaag | 1140 |
| catttgccaa gaatgttttc attaatcaag aacgaaagtc ggaggttcga agacgatcag | 1200 |
| ataccgtcgt agttccgacc ataaacgatg ccgaccggcg atgcggcggc gttattccca | 1260 |
| tgacccgccg ggcagcttcc gggaaaccaa agtctttggg ttccgggggg agtatggttg | 1320 |
| caaagctgaa acttaaagga attgacgaa gggcaccacc aggagtggag cctgcggctt | 1380 |
| aatttgactc aacacgggaa acctcacccg gcccggacac ggacaggatt gacagattga | 1440 |
| tagctctttc tcgattccgt gggtggtggt gcatggccgt tcttagttgg tggagcgatt | 1500 |
| tgtctggtta attccgataa cgaacgagac tctggcatgc taactagtta cgcgacccccc | 1560 |
| gagcggtcgg cgtcccccaa cttcttagag ggacaagtgg cgttcagcca cccgagattg | 1620 |
| agcaataaca ggtctgtgat gcccttagat gtccggggct gcacgcgcgc tacactgact | 1680 |
| ggctcagcgt gtgcctaccc tacgccggca ggcgcgggta acccgttgaa ccccattcgt | 1740 |
| gatgggggatc ggggattgca attattcccc atgaacgagg aattcccagt aagtgcgggt | 1800 |
| cataagcttg cgttgattaa gtccctgccc tttgtacaca ccgcccgtcg ctactaccga | 1860 |
| ttggatggtt tagtgaggcc ctcggatcgg ccccgccggg gtcggccac ggccctggcg | 1920 |
| gagcgctgag aagacggtcg aacttgacta tctagaggaa gtaaaagtcg taacaaggtt | 1980 |
| tccgtaggtg aacctgcgga aggatcatta acggagcccg gacggcggcc cgcggcggcg | 2040 |
| ccgcgccgcg cttccctccg cacacccacc ccccaccgc gacggcgcgt gcgggcgggg | 2100 |
| ccgtgcccgt tcgttcgctc gctcgttcgt tcgccgcccg gccgccgc gagagccgag | 2160 |
| aactcgggag ggagacgggg gagagagaga gagagagaga gagagagaga gagagagaga | 2220 |
| gaaagaaggg cgtgt | 2235 |

<210> SEQ ID NO 40
<211> LENGTH: 1969
<212> TYPE: DNA
<213> ORGANISM: Human
<220> FEATURE:
<221> NAME/KEY: misc_feature
<222> LOCATION: (57)..(61)
<223> OTHER INFORMATION: n is a, c, g, or t
      Human 18S rDNA sequence
<308> DATABASE ACCESSION NUMBER: GenBank No. M10098
<309> DATABASE ENTRY DATE: 1993-08-03

<400> SEQUENCE: 40

| | |
|---|---|
| ccgtccgtcc gtcgtcctcc tcgcttgcgg ggcgccgggc ccgtcctcga gccccnnnn | 60 |
| nccgtccggc cgcgtcgggg cctcgccgcg ctctacctac ctacctggtt gatcctgcca | 120 |
| gtagcatatg cttgtctcaa agattaagcc atgcatgtct aagtacgcac ggccggtaca | 180 |
| gtgaaactgc gaatggctca ttaaatcagt tatggttcct ttggtcgctc gctcctctcc | 240 |
| tacttggata actgtggtaa ttctagagct aatacatgcc gacgggcgct gaccccttc | 300 |

```
gcgggggga  tgcgtgcatt  tatcagatca  aaaccaaccc  ggtcagcccc  tctccggccc    360 cggccgggg   gcgggccgcg  gcggctttgg  tgactctaga  taacctcggg  ccgatcgcac    420 gcccccgtg   gcggcgacga  cccattcgaa  cgtctgccct  atcaactttc  gatggtagtc    480
gccgtgccta  ccatggtgac  cacgggtgac  ggggaatcag  ggttcgattc  cggagaggga    540
gcctgagaaa  cggctaccac  atccaaggaa  ggcagcaggc  gcgcaaatta  cccactcccg    600
acccggggag  gtagtgacga  aaaataacaa  tacaggactc  tttcgaggcc  ctgtaattgg    660
aatgagtcca  ctttaaatcc  tttaacgagg  atccattgga  gggcaagtct  ggtgccagca    720
gccgcggtaa  ttccagctcc  aatagcgtat  attaaagttg  ctgcagttaa  aaagctcgta    780
gttggatctt  gggagcgggc  gggcggtccg  ccgcgaggcg  agccaccgcc  cgtccccgcc    840
ccttgcctct  cggcgccccc  tcgatgctct  tagctgagtg  tcccgcgggg  cccgaagcgt    900
ttactttgaa  aaaattagag  tgttcaaagc  aggcccgagc  cgcctggata  ccgcagctag    960
gaataatgga  ataggaccgc  ggttctattt  tgttggtttt  cggaactgag  gccatgatta   1020
agagggacgg  ccgggggcat  tcgtattgcg  ccgctagagg  tgaaattctt  ggaccggcgc   1080
aagacggacc  agagcgaaag  catttgccaa  gaatgttttc  attaatcaag  aacgaaagtc   1140
ggaggttcga  agacgatcag  ataccgtcgt  agttccgacc  ataaacgatg  ccgaccggcg   1200
atgcggcggc  gttattccca  tgacccgccg  ggcagcttcc  gggaaaccaa  agtctttggg   1260
ttccgggggg  agtatggttg  caaagctgaa  acttaaagga  attgacgaa   gggcaccacc   1320 aggagtggag  cctgcggctt  aatttgactc  aacacgggaa  acctcacccg  gcccggacac   1380
ggacaggatt  gacagattga  tagctctttc  tcgattccgt  gggtggtggt  gcatggccgt   1440
tcttagttgg  tggagcgatt  tgtctggtta  attccgataa  cgaacgagac  tctggcatgc   1500
taactagtta  cgcgacccc   gagcggtcgg  cgtcccccaa  cttcttagag  ggacaagtgg   1560
cgttcagcca  cccgagattg  agcaataaca  ggtctgtgat  gcccttagat  gtccggggct   1620
gcacgcgcgc  tacactgact  ggctcagcgt  gtgcctaccc  tacgccggca  ggcgcgggta   1680
acccgttgaa  ccccattcgt  gatggggatc  ggggattgca  attattcccc  atgaacgagg   1740
aattcccagt  aagtgcgggt  cataagcttg  cgttgattaa  gtccctgccc  tttgtacaca   1800
ccgcccgtcg  ctactaccga  ttggatggtt  tagtgaggcc  ctcggatcgg  ccccgccggg   1860
gtcggcccac  ggcctggcgg  agcgctgaga  agacggtcga  acttgactat  ctagaggaag   1920
taaaagtcgt  aacaaggttt  ccgtaggtga  acctgcggaa  ggatcatta                1969
```

RIBOSOMAL POLYNUCLEOTIDES AND RELATED EXPRESSION SYSTEMS

REFERENCE TO PRIORITY DOCUMENTS

This application claims the benefit of priority under 35 U.S.C. §119(e) of U.S. Provisional Patent Application Ser. No. 61/649,453, filed May 21, 2012 and U.S. Provisional Patent Application Ser. No. 61/778,194, filed Mar. 12, 2013. Priority of the aforementioned filing dates is hereby claimed and the disclosures of the provisional patent applications are hereby incorporated by reference in their entirety.

STATEMENT CONCERNING GOVERNMENT SUPPORT

This invention was made with government support under GM078071 awarded by the National Institutes of Health. The government has certain rights in the invention.

INCORPORATION OF SEQUENCE LISTING

This application contains an electronic equivalent paper copy of the sequence listing submitted herewith electronically via EFS web and a computer-readable form of the sequence listing submitted herewith electronically via EFS web and contains the file named "37651506001USSequenceListing.txt," which is 30,874 bytes in size and which was created on May 20, 2013, are hereby incorporated by reference in their entirety.

BACKGROUND

Ribosomes are macromolecular structures that catalyze protein synthesis in cells. They consist universally of two subunits composed of numerous proteins and several RNAs. Proteins contribute to the structure, stability, and activity of the subunits. However, in general, it has been difficult to assign specific functions to individual ribosomal proteins, as many are not essential for ribosomal function or have additional extraribosomal functions. By contrast, ribosomal RNAs (rRNAs) are responsible for the overall shape of the ribosomal subunits as well as for the enzymatic activity that catalyzes protein synthesis. Evidence is accumulating that rRNAs may also affect other aspects of protein synthesis, including mRNA recruitment, regulation of the efficiency of translation of specific mRNAs, and facilitation of ribosomal shunting.

The ability to study the role of rRNA in ribosome assembly, protein synthesis, and non-canonical aspects of rRNA function requires being able to alter rRNA sequences and monitor the activity of modified ribosomal subunits in vivo. Analysis of rRNA processing, ribosome assembly, and function of higher eukaryotic rRNA have been hindered by the lack of an expression system that enables rRNA to be modified and then examined functionally.

There is a great need in the art for effective systems for expressing modified rRNAs and performing functional analyses, especially mammalian systems.

SUMMARY

In one aspect, provided are synthetic or isolated polynucleotides encoding a mammalian 18S rRNA that is resistant to pactamycin. In these polynucleotides, the pactamycin-resistance is conferred by one or more single residue substitutions in the 18S rRNA sequence. Also provided are fragments of such polynucleotides harboring the substitutions, complementary sequences, and substantially identical sequences. In some embodiments, the single residue substitution in the polynucleotide conferring pactamycin-resistance is at a position corresponding to G963, A964, C1065 or C1066 of mouse 18S rRNA (SEQ ID NO:23). In some preferred embodiments, the single residue substitution is at a position corresponding to position G963 of SEQ ID NO:23. Some of these polynucleotides contain a single residue substitution that corresponds to a G963A substitution in SEQ ID NO:23.

In some embodiments, the polynucleotide encodes a pactamycin resistant human 18S rRNA or mouse 18S rRNA. In some embodiments, the polynucleotide includes SEQ ID NO:23 except for a G963A substitution. In some related aspects, provided are mammalian 18S rRNA molecules encoded by the synthetic or isolated polynucleotides. In another aspect, provided are vectors harboring the polynucleotides that encode a pactamycin resistant 18S rRNA. In some of these vectors, the polynucleotide can further include the 5' ETS and ITS1 of the rDNA sequence. In some embodiments, the vectors further include a pol-I promoter or a cytomegalovirus (CMV) promoter. In some embodiments, the vectors further include the 3' ETS or an SV40 poly(A) signal. In another related aspect, host cells that harbor an expression vector are disclosed herein.

In another aspect, provided are methods for identifying a mutation in 18S rRNA that alters ribosomal functions. The methods entail (a) introducing an additional mutation to a synthetic polynucleotide encoding a mammalian 18S rRNA that is resistant to pactamycin, wherein the pactamycin-resistance is conferred by one or more single residue substitutions in the 18S rRNA sequence, (b) expressing the synthetic polynucleotide bearing the additional mutation in a host cell in the presence of pactamycin, and (c) detecting an alteration in the ribosomes of the host cell relative to that of a control cell expressing the synthetic polynucleotide without the additional mutation. These steps allow identification of the additional mutation as one altering ribosomal functions. Typically, the synthetic polynucleotide is present in an expression vector introduced into the host cell. In some embodiments, the pactamycin-resistant 18S rRNA harbors a single residue substitution at a position corresponding to G963, A964, C1065 or C1066 of mouse 18S rRNA (SEQ ID NO:23). For example, the 18S rRNA can harbor a substitution corresponding to a G963A substitution in SEQ ID NO:23. Some methods employ a synthetic polynucleotide comprising SEQ ID NO:23 except for a G963A substitution.

In another aspect, provided are methods for producing ribosomes with enhanced translation efficiency in a mammalian cell. These methods entail (a) introducing an additional mutation to a synthetic polynucleotide encoding a pactamycin-resistance mammalian 18S rRNA, wherein the pactamycin-resistance is conferred by one or more single residue substitutions in the 18S rRNA sequence, (b) introducing the synthetic polynucleotide bearing said additional mutation into a host mammalian cell, (c) culturing the cell in the presence of pactamycin, and (d) detecting enhanced translation efficiency in the cell relative to that of a control cell expressing the synthetic polynucleotide without the additional mutation. With these methods, ribosomes with enhanced translation efficiency can be obtained. Typically, the synthetic polynucleotide employed in these methods is present in an expression vector introduced into the host cell. In some embodiments, the pactamycin-resistant 18S rRNA harbors a single residue substitution at position corresponding to G963, A964, C1065 or C1066 of mouse 18S rRNA (SEQ ID NO:23). Some of the methods employ a 18s rRNA-encoding synthetic polynucleotide with a single residue substitution that corresponds to a G963A substitution in SEQ ID NO:23. For example, the methods can utilize a synthetic polynucleotide that includes SEQ ID NO:23 except for a G963A substitution. In various embodiments, translation efficiency can be determined by measuring the level of a specific polypeptide in the host cell.

In another aspect, provided is a kit comprising an expression vector comprising a synthetic polynucleotide encoding a mammalian 18S rRNA that is resistant to pactamycin, wherein the pactamycin-resistance is conferred by one or more single residue substitutions in the 18S rRNA sequence, as described herein. In one embodiment, the kit further includes a cell containing the expression vector.

In another aspect, provided is a method for preferentially translating a recombinant mRNA, the method comprising expressing in a mammalian cell a polynucleotide encoding a mammalian 18S rRNA that is resistant to pactamycin, wherein the polynucleotide encoding the 18S rRNA has been further altered to introduce one or more additional mutations, the one or more additional mutations conferring preferential binding of the recombinant mRNA to the 18S rRNA encoded by the polynucleotide, the method further comprising providing the recombinant mRNA to the cell and exposing the cell to pactamycin in an amount sufficient to reduce or eliminate protein synthesis from the cell's endogenous 40S ribosomal subunits, thereby largely restricting protein synthesis in the cell to 40S ribosomal subunits comprising the 18S rRNA encoded by the polynucleotide and preferentially translating the recombinant mRNA.

A further understanding of the nature and advantages of the systems, methods and kits described herein may be realized by reference to the remaining portions of the specification and claims.

DETAILED DESCRIPTION

I. Overview

Figure 1:
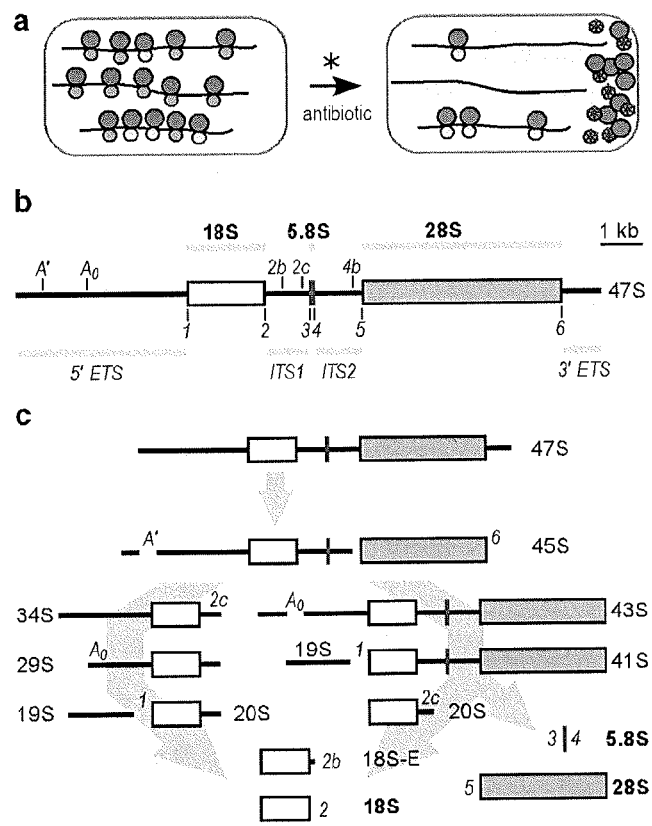
FIGS. 1a-1c show rRNA transcript processing pathway and an rRNA expression system according to one implementation. (a) A schematic representation of an rRNA expression platform. Grey enclosures represent cells and contain polysomes with mRNA indicated as black lines and ribosomal subunits as circles (60S subunits as larger circles; 40S subunits as smaller circles). The darker colored 40S subunits are antibiotic-sensitive endogenous subunits; the white 40S subunits contain synthetic 18S rRNA and are antibiotic-resistant. The different colors are used to indicate that the subunits are physically distinguishable. A cell-permeable antibiotic binds to and blocks the activity of endogenous 40S subunits. Synthetic 40S subunits are unaffected and are able to translate under these conditions. (b) Mouse 47S primary rRNA transcript. 47S rRNA is indicated schematically as a horizontal line. The different sections represent encoded rRNAs. The 18S rRNA is the RNA component of 40S ribosomal subunits and the 28S and 5.8S rRNAs are RNA components of 60S subunits. The black lines represent the external transcribed spacer regions (5' ETS and 3' ETS) and the internal transcribed spacer regions (ITS1 and ITS2), as indicated. Cleavage sites in the transcribed spacers are indicated as vertical lines and labeled. (c) rRNA transcript processing pathways. Processing of the precursor transcripts involves numerous protein and RNA factors and has been studied extensively in various organisms. The mouse 47S precursor rRNA is transcribed in the nucleolus by RNA polymerase I, and is subsequently processed by two possible pathways. Cleavage proceeds in the direction of the arrows from 47S to 18S, 5.8S, and 28S rRNAs; 45S rRNA can be processed to 18S rRNA by two pathways as indicated, which generate different intermediate products. Processing sites and major cleavage products resulting from maturation of 18S rRNA are indicated at each cleavage step. Processing of 5.8S and 28S rRNAs involve additional cleavage steps and intermediate products, which are not indicated.

Described herein are mouse 18S rRNA expression systems and methods of use. This rRNA is the RNA component of the small (40S) ribosomal subunit and is co-transcribed as part of a larger precursor transcript along with the 5.8S and 28S rRNAs, which are components of the large (60S) subunit (FIG. 1b). A sequence tag was introduced into the 18S rRNA that can be detected by hybridization allowing for the study of transcription, processing, and subcellular distribution of 40S subunits containing synthetic rRNAs. To monitor the translational activity of the ribosomal subunits, mutations were identified in the 18S rRNA that confer resistance to inhibition by the antibiotic pactamycin. Pactamycin is thought to inhibit translation by binding to the E site in 40S ribosomal subunits, blocking translocation of the mRNA-tRNA complex through the ribosome during elongation. Therefore, by expressing 18S rRNAs with a pactamycin-resistance mutation in cells, the drug can be used to specifically block translation from the cell's endogenous 40S subunits and monitor translation from subunits containing the pactamycin-resistant mutation.

Provided herein is a mammalian 18S rRNA expression system. The expression system can harbor a sequence tag which is inserted into expansion segment 3 of mouse 18S rRNA to monitor expression and cleavage by hybridization. The expression system can typically also harbor a single residue substitution in the 18S rRNA coding region that confers resistance to pactamycin, allowing functional analysis of 40S ribosomal subunits containing synthetic 18S rRNAs by selectively blocking translation from endogenous (pactamycin-sensitive) subunits. With such an expression system, rRNA constructs can be suitably expressed in transfected cells, shown to process correctly, incorporate into ≈15% of 40S subunits, and function normally based on various criteria.

The correct processing of modified 18S rRNA in the expression system described herein can provide a method to examine any implications on rRNA processing and ribosome functions of mutations or natural variations in 18S rRNA sequence, and can also be used to investigate the importance of sequences flanking the 18S rRNA in precursor transcripts. For example, and as detailed in the Examples below, e.g., the effect of the 5' external transcribed spacer (ETS) and the first internal transcribed spacer (ITS1) in the 18S rRNA expression system was analyzed. Specifically, while deletion analysis supported the requirement of binding sites for the U3 snoRNA, it showed that a large segment of the 5' external transcribed spacer and the entire first internal transcribed spacer, both of which flank 18S rRNA, are not required for translation from or assembly of mature subunits.

In accordance with these studies, provided herein are synthetic polynucleotides and related expression vectors which are useful for expressing mammalian 18S rRNA and analyzing ribosome functions. Also provided herein are methods for identifying mutations in rRNAs or ribosome proteins that cause abnormal ribosome functions. Further provided herein are methods for evolving ribosomal rRNA sequences to produce ribosomes with modified properties, e.g., enhanced translation activities. The subject matter described herein find various applications in basic research and synthetic biology.

It should be appreciated that the subject matter described herein should not be limited to the particular methodology, protocols, and reagents described as these may vary. Unless otherwise indicated, the practice of the described implementations employ conventional techniques of molecular biology (including recombinant techniques), microbiology, cell biology, biochemistry and immunology, which are within the skill of the art. For example, exemplary methods are described in the following references, Sambrook et al., *Molecular Cloning: A Laboratory Manual*, Cold Spring Harbor Press (3$^{rd}$ ed., 2001); Brent et al., *Current Protocols in Molecular Biology*, John Wiley & Sons, Inc. (ringbou ed., 2003); Freshney, *Culture of Animal Cells: A Manual of Basic Technique*, Wiley-Liss, Inc. (4$^{th}$ ed., 2000); and Weissbach & Weissbach, *Methods for Plant Molecular Biology*, Academic Press, NY, Section VIII, pp. 421-463, 1988.

II. Definitions

Unless defined otherwise, all technical and scientific terms used herein have the same meaning as commonly understood by those of ordinary skill in the art. The following references provide one of skill with a general definition of many of the terms used herein: *Academic Press Dictionary of Science and Technology*, Morris (Ed.), Academic Press (1$^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3$^{rd}$ ed., 2002); *Dictionary of Chemistry*, Hunt (Ed.), Routledge (1$^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology (Oxford Paperback Reference)*, Martin and Hine (Eds.), Oxford University Press (4$^{th}$ ed., 2000). Further clarifications of some of these terms as they apply specifically to this disclosure are provided herein.

As used herein, the singular forms "a", "an", and "the" include plural reference unless the context clearly dictates otherwise. Thus, for example, reference to "a cell" includes a plurality of such cells, reference to "a protein" includes one or more proteins and equivalents thereof known to those skilled in the art, and so forth.

Eukaryotes ribosomes are 80S, consisting of a small (40S) and large (60S) subunit. Their 40S subunit has an 18S RNA (1900 nucleotides) and ≈33 proteins. The large subunit is composed of a 5S RNA (≈120 nucleotides), 28S RNA (≈4700 nucleotides), a 5.8S RNA (≈160 nucleotides) subunits and ≈49 proteins. Ribosomes synthesize proteins according to the information encoded in mRNA. During this process, both the incoming amino acid and the nascent peptide are bound to tRNA molecules. The ribosome contains three RNA binding sites, designated A, P and E. The A-site binds an aminoacyl-tRNA (a tRNA bound to an amino acid); the P-site binds a peptidyl-tRNA (a tRNA bound to the peptide being synthesized); and the E-site binds a free tRNA before it exits the ribosome. Conventionally, protein synthesis begins at a start codon AUG near the 5' end of the mRNA. The initiation codon of mRNA binds to the P-site of the ribosome first.

The ribosomal DNA (rDNA) consists of a tandem repeat of a unit segment, an operon, composed of nontranscribed spacer (NTS), 5' external transcribed spacer (5' ETS), 18S, internal transcribed spacer 1 (ITS1), 5.8S, internal transcribed spacer 2 (ITS2), 28S, and the 3' external transcribed spacer (3' ETS) sequence elements. The rDNA is first transcribed into a polycistronic rRNA precursor transcript. During rRNA maturation, ETS and ITS pieces are excised and as non-functional maturation by-products rapidly degraded. The 5' external transcribed spacer (5' ETS) is critical for 18S rRNA formation and is the longest noncoding region in a ribosomal RNA transcript in higher eukaryotes.

The phrase "polynucleotide of interest" (or "gene of interest" or "target gene") is intended to include a cistron, an open reading frame (ORF), or a polynucleotide sequence which codes for a polypeptide or protein product ("polypeptide of interest" or "target polypeptide"). For enhanced expression of a polypeptide of interest, a polynucleotide of interest encoding the polypeptide can be introduced into a host cell bearing a modified 18S rRNA expression system as described herein.

In particular, the 18S rRNA is modified (e.g., with random or targeted mutagenesis) to identify altered 18S rRNA that leads to enhanced translation of the polypeptide of interest. For expression the polypeptide, the polynucleotide of interest is typically present in an expression vector which additionally contain appropriate transcription regulatory elements (e.g., promoter sequences) operably linked to the coding sequence. In accordance with some implementations, various polypeptides of interest are suitable for enhanced expression with methods described herein, e.g., therapeutic proteins, nutritional proteins and industrially useful proteins.

The term "endogenous" as used herein refers to a polynucleotide or polypeptide that is normally found in the wild-type host, while the term "exogenous" refers to a polynucleotide or polypeptide that is not normally found in the wild-type host.

A "host cell" refers to a living cell into which a heterologous polynucleotide sequence is to be or has been introduced. The living cell includes both a cultured cell and a cell within a living organism. Means for introducing the heterologous polynucleotide sequence into the cell are well known, e.g., transfection, electroporation, calcium phosphate precipitation, microinjection, transformation, viral infection, and/or the like. Often, the heterologous polynucleotide sequence to be introduced into the cell is a replicable expression vector or cloning vector. In some embodiments, host cells can be engineered to incorporate a desired gene on its chromosome or in its genome. Many host cells that can be employed (e.g., CHO cells) serve as hosts are well known in the art. See, e.g., Sambrook et al., *Molecular Cloning: A Laboratory Manual*, Cold Spring Harbor Press ($3^{rd}$ ed., 2001); and Brent et al., *Current Protocols in Molecular Biology*, John Wiley & Sons, Inc. (ringbou ed., 2003). In some preferred embodiments, the host cell is a mammalian cell.

The term "nucleotide sequence," "nucleic acid sequence," "nucleic acid," or "polynucleotide sequence," refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. Nucleic acid sequences can be, e.g., prokaryotic sequences, eukaryotic mRNA sequences, cDNA sequences from eukaryotic mRNA, genomic DNA sequences from eukaryotic DNA (e.g., mammalian DNA), and synthetic DNA or RNA sequences, but are not limited thereto.

The term "operably linked" or "operably associated" refers to functional linkage between genetic elements that are joined in a manner that enables them to carry out their normal functions. For example, a gene is operably linked to a promoter when its transcription is under the control of the promoter and the transcript produced is correctly translated into the protein normally encoded by the gene. Similarly, a translational enhancer element is operably associated with a gene of interest if it allows up-regulated translation of a mRNA transcribed from the gene.

Screening is, in general, a two-step process in which one first determines which cells do and do not express a screening marker or harbor a functional or phenotypic property, and then physically separates the cells having the desired property. Selection is a form of screening in which identification and physical separation are achieved simultaneously by expression of a selection marker and/or detection of a functional/phenotypic characteristic. For example, in some genetic circumstances, selection allows cells expressing the marker to survive while other cells die (or vice versa). As used herein, screening and selection refer to the process of generating one or more (e.g., a library of) candidate variants of a reference molecule (e.g., 18S rDNA) and then identifying from the candidate variants one or more specific variants that harbor a desired structure or function (e.g., enhanced translation efficiency).

A "substantially identical" nucleic acid or amino acid sequence refers to a polynucleotide or amino acid sequence which can include a sequence that has at least 75%, 80% or 90% sequence identity to a reference sequence as measured by one of the well-known programs described herein (e.g., BLAST) using standard parameters. The sequence identity is preferably at least 95%, more preferably at least 98%, and most preferably at least 99%. In some embodiments, the subject sequence is of about the same length as compared to the reference sequence, i.e., consisting of about the same number of contiguous amino acid residues (for polypeptide sequences) or nucleotide residues (for polynucleotide sequences).

Sequence identity can be readily determined with various methods known in the art. For example, the BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)). Percentage of sequence identity is determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

A cell has been "transformed" or "transfected" by exogenous or heterologous polynucleotide when such polynucleotide has been introduced inside the cell. The transforming polynucleotide may or may not be integrated (covalently linked) into the genome of the cell. In prokaryotes, yeast, and mammalian cells for example, the transforming polynucleotide may be maintained on an episomal element such as a plasmid. With respect to eukaryotic cells, a stably transformed cell is one in which the transforming polynucleotide has become integrated into a chromosome so that it is inherited by daughter cells through chromosome replication. This stability is demonstrated by the ability of the eukaryotic cell to establish cell lines or clones having a population of daughter cells containing the transforming polynucleotide. A "clone" is a population of cells derived from a single cell or common ancestor by mitosis. A "cell line" is a clone of a primary cell that is capable of stable growth in vitro for many generations.

The term "vector" or "construct" refers to polynucleotide sequence elements arranged in a definite pattern of organization such that the expression of genes/gene products that are operably linked to these elements can be predictably controlled. Typically, they are transmissible polynucleotide sequences (e.g., plasmid or virus) into which a segment of foreign polynucleotide sequence can be spliced in order to introduce the foreign DNA into host cells to promote its replication and/or transcription.

A cloning vector is a polynucleotide sequence (typically a plasmid or phage) which is able to replicate autonomously in a host cell, and which is characterized by one or a small number of restriction endonuclease recognition sites. A foreign polynucleotide sequence fragment may be spliced into the vector at these sites in order to bring about the replication and cloning of the fragment. The vector may contain one or more markers suitable for use in the identification of transformed cells. For example, markers may provide tetracycline or ampicillin resistance.

An expression vector is similar to a cloning vector but is capable of inducing the expression of the polynucleotide sequence that has been cloned into it, after transformation into a host. The cloned polynucleotide sequence is usually placed under the control of (i.e., operably linked to) certain regulatory sequences such as promoters or enhancers. Promoter sequences may be constitutive, inducible or repressible.

III. Ribosomal Polynucleotides for Expressing Mammalian 18S rRNA

Provided herein are synthetic (isolated or modified) ribosomal polynucleotides or nucleic acid molecules for studying mammalian 18S rRNA expression and related ribosome activities. The ribosomal polynucleotides described herein encompass rDNA and rRNA nucleotide sequences described herein, as well as combinations or substantially identical variants thereof. In some embodiments, the polynucleotide encodes (for DNA sequence) or includes (for RNA sequence) the full length or part of a mammalian (e.g., mouse or human) 18S rRNA nucleotide sequence, or a substantially identical variant thereof. In some embodiments, the polynucleotide encodes or includes the full length or part of SEQ ID NO: 23 with one or more specific substitutions described herein, or a substantially identical variant thereof. In some of these embodiments, the synthetic polynucleotides can include a fragment of the full length 18S rDNA or rRNA sequence and harbor one or more of the specific substitutions. Thus, the ribosomal polynucleotides described herein can include a mammalian (e.g., mouse or human) rRNA nucleotide sequence, rDNA nucleotide sequence, or a pre-rRNA nucleotide sequence, fragments thereof, or a substantially identical variant of the foregoing.

In one aspect, provided are isolated or synthetic ribosomal polynucleotides which can include or encode a pactamycin resistant 18S rRNA or a fragment thereof. In some preferred embodiments, the encoded pactamycin resistant 18S rRNA is a mammalian 18S rRNA. The pactamycin resistance is typically conferred by one or more single residue substitutions or mutations at several specific conserved residues at the E-site of the encoded 18S rRNA. Using mouse 18S rDNA sequence (SEQ ID NO:23) (Accession No. JQ247698) as the reference sequence, these residues include G963, A964, C1065 and C1066. Some embodiments described herein are directed to ribosomal polynucleotides or "synthetic polynucleotides" which include or encode a pactamycin resistant mammalian 18S rRNA. These polynucleotides typically include a mammalian 18S rDNA sequence with one or more mutations at positions corresponding to positions G963, A964, C1065 and C1066 in mouse 18S rDNA sequence (SEQ ID NO:23), a substantially identical sequence, or a subsequence thereof encompassing the substitutions or mutations.

As the above-noted residues for substitutions are conserved among different mammalian species, one can readily determine (e.g., via sequence alignment) the exact positions of these residues in other mammalian species. Thus, as used herein, nucleotide residues or positions corresponding to G963, A964, C1065 and C1066 in mouse 18S rDNA sequence (SEQ ID NO:23) encompass these conserved residues present in any polynucleotide sequences encoding a mammalian 18S rRNA or complementary sequences. For example, the corresponding residues in another mouse 18S rDNA sequence, Accession No. X00686 (SEQ ID NO: 34; Raynal et al., FEBS Lett. 167:263-268, 1984), are G962, A963, C1064 and C1065, respectively. Similarly, the corresponding residues in human 18S rDNA sequence (SEQ ID NO:24) (McCallum et al. Biochem. J. 1985; 232:725-733, 1985; Accession No. X03205) are G961, A962, C1063 and C1064, respectively. The exact positions of these conserved residues in various other mammalian 18S rRNA or rDNA sequences can also be readily determined. These include, e.g., mouse 18S rDNA sequence (Accession No. NR_003278; SEQ ID NO: 35), rat 18S rDNA sequences (Accession Nos. X01117 SEQ ID NO: 36; and M11188 SEQ ID NO: 37), rabbit 18S rDNA sequence (Accession No. X06778, SEQ ID NO: 38), and human 18S rDNA sequences (Accession Nos. K03432, SEQ ID NO: 39; and M10098, SEQ ID NO: 40)

In some embodiments, the ribosomal polynucleotides described herein can include or encode the full length mammalian 18S rRNA with one or more of the specific substitutions conferring pactamycin resistance described herein. In some other embodiments, the synthetic polynucleotides can include or encode 50 or fewer consecutive nucleotides of the mammalian 18S rRNA which encompasses one or more of the specific substitutions conferring pactamycin resistance. In some other embodiments, the polynucleotides include or encode 100 or fewer consecutive nucleotides of the mammalian 18S rRNA including one or more of the specific substitutions. In still some other embodiments, the polynucleotides include or encode 250, 500, 750, 1000, 1500 or more consecutive nucleotides of the mammalian 18S rRNA, including one or more of the above-described specific substitutions conferring pactamycin resistance. In any of these embodiments, the synthetic polynucleotides can also encompass substantially identical sequences or complementary sequences of the full length 18S rRNA sequences or fragment sequences described herein.

In some other embodiments, the polynucleotides include, or is complementary to, a sequence that is at least 80%, 90%, 95% or 99% identical to SEQ ID NO:23 and contains one or more substitutions at positions corresponding to positions G963, A964, C1065 and C1066 of SEQ ID NO:23. In some of these embodiments, the mutation is at a position corresponding to position G963 of SEQ ID NO:23. For example, the polynucleotides can include or encode an 18S rRNA sequence with a G→A substitution at a position corresponding to G963 of SEQ ID NO:23. In some embodiments, the polynucleotides include a sequence that is identical or complementary to mouse 18S rDNA or human 18S rDNA sequence except for one or more specific substitutions described herein. As noted above, the synthetic polynucleotides described herein also encompass fragments of these sequences which harbor one or more of the specific substitutions.

The ribosomal polynucleotides described herein can be single-stranded, double-stranded, triplex, linear or circular. They can include one or more nucleotide derivatives or analogs of the foregoing (e.g., 1, 2, 3, 4, 5, 6, 7, 8, 9, 10 or more analog or derivative nucleotides). In some embodiments, the polynucleotide is entirely comprised of one or more analog or derivative nucleotides, and sometimes the polynucleotide is composed of about 50% or fewer, about 25% or fewer, about 10% or fewer or about 5% or fewer analog or derivative nucleotide bases. One or more nucleotides in an analog or derivative nucleic acid may include a nucleobase modification or backbone modification, such as a ribose or phosphate modification (e.g., ribose peptide nucleic acid (PNA) or phosphothioate linkages), as compared to a RNA or DNA nucleotide. Nucleotide analogs and derivatives are known to the person of ordinary skill in the art, and non-limiting examples of such modifications are set forth in U.S. Pat. Nos. 4,469,863; 5,536,821; 5,541,306; 5,637,683; 5,637,684; 5,700,922; 5,717,083; 5,719,262; 5,739,308; 5,773,601; 5,886,165; 5,929,226; 5,977,296; 6,140,482; 6,455,308; and in WIPO publications WO 00/56746 and WO 01/14398. Methods for synthesizing nucleic acids comprising such analogs or derivatives are also described in the art, e.g., in the patent publications cited above, and also in U.S. Pat. Nos. 6,455,308; 5,614,622; 5,739,314; 5,955,599; 5,962,674; 6,117,992; and WO 00/75372.

IV. Vectors for Expressing Pactamycin Resistant 18S rRNA

The polynucleotides encoding mammalian 18S rRNA described herein can be incorporated into an expression vector for introducing into a mammalian host cell. These vectors are typically circular and, in addition to the 18S rRNA-encoding polypeptide, can also contain selectable markers, an origin of replication, and other elements. For example, the vector can contain a selection marker. The selection marker allows one to select for cells into which the vector has been introduced and/or stably integrated. In some embodiments, the selection marker can be a polynucleotide encoding a protein or enzyme that confers to the cells visually identifiable characteristics. For example, as exemplified herein, the vector can harbor a selection marker encoding *Renilla* luciferase reporter enzyme. Other examples include jellyfish green fluorescent protein (GFP) and bacterial β-galactosidase. In some other embodiments, the selection marker for identifying host cells into which the vector was introduced and/or stably integrated can be an antibiotic resistance gene. Examples of such markers include antibiotic resistance genes for neomycin, chloramphenicol, blasticidin, hygromycin, and zeocin.

In addition to the sequence encoding pactamycin-resistant 18S rRNA, the vector can also bear other rDNA sequences that may be necessary for proper rRNA transcription and processing, as well as proper ribosome assembly and function. For example, some vectors described herein can additionally harbor sequences corresponding to the 5'-ETS and ITS elements of the precursor rRNA sequence. A specific vector for expressing pactamycin-resistant mammalian 18S rRNA is exemplified in the Examples below (e.g., Example 4).

One more component of the expression vector is an origin of replication. Replication origins are unique DNA segments that contain multiple short repeated sequences that are recognized by multimeric origin-binding proteins and that play a key role in assembling DNA replication enzymes at the origin site. Suitable origins of replication for use in the vectors described herein include, e.g., EBV oriP, SV40, *E. coli* oriC, colE1 plasmid origin, ARS, and the like. Another useful element in an expression vector is a multiple cloning site or polylinker. Synthetic DNA encoding a series of restriction endonuclease recognition sites is inserted into a plasmid vector, for example, downstream of the promoter element. These sites are engineered for convenient cloning of DNA into the vector at a specific position.

The polynucleotides or vectors for expressing modified 18S rRNA herein can be readily constructed in accordance with methodologies known in the art of molecular biology in view of the teachings of the specification. See, e.g., Sambrook et al., *Molecular Cloning: A Laboratory Manual*, Cold Spring Harbor Press ($3^{rd}$ ed., 2001); Brent et al., *Current Protocols in Molecular Biology*, John Wiley & Sons, Inc. (ringbou ed., 2003); and Freshney, *Culture of Animal Cells: A Manual of Basic Technique*, Wiley-Liss, Inc. ($4^{th}$ ed., 2000). Typically, the expression vectors are assembled by inserting into a suitable vector backbone the polynucleotide encoding a pactamycin resistant 18S rRNA, sequences encoding selection markers, and other optional elements described herein. To generate the vectors, the above-described polynucleotides can be inserted into various known plasmids for transfecting mammalian host cells. Such known plasmids include, e.g., pRL-CMV (Promega), BPV, EBV, vaccinia virus based vector, SV40, 2-micron circle, pcDNA3.1, pcDNA3.1/GS, pYES2/GS, pMT, p IND, pIND(Sp1), pVgRXR (Invitrogen), and the like, or their derivatives. These plasmids are all described and well known in the art (Botstein et al., Miami Wntr. SyTnp. 19:265-274, 1982; Broach, In: *The Molecular Biology of the Yeast Saccharomyces: Life Cycle and Inheritance*, Cold Spring Harbor Laboratory, Cold Spring Harbor, N.Y., p. 445-470, 1981; Broach, Cell 28:203-204, 1982; Dilon et at., J. Clin. Hematol. Oncol. 10:39-48, 1980; and Maniatis, In: *Cell Biology: A Comprehensive Treatise, Vol. 3, Gene Sequence Expression*, Academic Press, NY, pp. 563-608, 1980.

V. Host Cells Expressing Pactamycin Resistant 18S rRNA

Provided are engineered mammalian cells which express pactamycin resistant 18S rRNA. Using the polynucleotide molecules or expression vectors described above, various mammalian cells can be employed for introducing an expression vector as described herein or by stably integrating the rDNA described herein into the host genome. The polynucleotides encoding pactamycin-resistant 18S rRNA or expression vectors described above can be introduced into an appropriate host cell (e.g., a mammalian cell such as mouse N2a cell or CHO cell) by any means known in the art. The cells can transiently or stably express the pactamycin resistant 18S rRNA.

Preferably, host cells for expressing the mammalian 18S rRNA as described herein are eukaryotic cells, e.g., mammalian cells. Eukaryotic vector/host systems, and preferably mammalian expression systems, allow for proper post-translational modifications of expressed mammalian proteins to occur, e.g., proper processing of the primary transcript, glycosylation, phosphorylation and advantageously secretion of expressed product. Therefore, eukaryotic cells such as mammalian cells are the preferred host cells for introducing the polynucleotides or expression vectors described above. One specific example is mouse Neuro 2a (N2a) cell as detailed in the Examples below. Other suitable cells include both animal cells (such as cells from insect, rodent, cow, goat, rabbit, sheep, non-human primate, human, and the like) and plant cells (such as rice, corn, cotton, tobacco, tomato, potato, and the like). Other specific examples of such host cell lines include CHO, BHK, HEK293, VERO, HeLa, COS, MDCK, and W138.

Other than mammalian cells, the host cell for expressing synthetic 18S rRNA as described herein may also be a yeast cell or a plant cell. Yeast or plant cells suitable for stable integration and expression of a transgene may be employed in these applications via introducing the 18S rRNA-encoding polynucleotide into the host via a yeast or plant expression vector. Examples of suitable insect cells include cells from *Drosophila larva*. When insect cells are used, the polynucleotide can be introduced into the cells via appropriate expression vectors. For example, baculovirus vectors can be employed as described in the art (Jasny, Science 238:1653, 1987; and Miller et al., In: *Genetic Engineering* (1986), Setlow, J. K., et al., eds., Plenum, Vol. 8, pp. 277-297). When insect cells are employed as hosts, the *Drosophila*-alcohol dehydrogenase promoter may optionally be used in the expression vector for introducing the polynucleotide (Rubin, Science 240:1453-1459, 1988).

Any convenient protocol may be employed for in vitro or in vivo introduction of the vector expressing a pactamycin resistant 18S rRNA into the host cell, depending on the location of the host cell. In some embodiments, the expression vector is transiently transfected into a host cell (e.g., a cultured cell line such as N2a), as exemplified in the Examples below. This can be accomplished with routinely practiced methods, e.g., by following the protocols exemplified herein. In some other embodiments, the expression vector may be stably integrated into the host genome. Typically, after appropriate restriction enzyme digestion to generate free ends of homology to the host chromosome, the polynucleotide can then be transfected into host cells. The expression vectors can be introduced into the host cell by standard protocols routinely practiced in the art. For example, the vector can be transfected into the host cell by calcium phosphate co-precipitation, by conventional mechanical procedures such as microinjection or electroporation, by insertion of a plasmid encased in liposomes, and by virus vectors. These techniques are all well-known and routinely practiced in the art, e.g., Freshney, supra; Sambrook et al., supra; and Brent et al., supra). Host cells which harbor the transfected recombinant expression vector can be identified and isolated using the selection marker present on the vector. Large numbers of recipient cells may then be grown in a medium which selects for vector-containing cells.

In some embodiments, where the host cell is an isolated cell, the expression vector may be introduced directly into the cell under cell culture conditions permissive of viability of the host cell, e.g., by using standard transformation techniques. Such techniques include, but are not necessarily limited to: viral infection, transfection, conjugation, protoplast fusion, electroporation, particle gun technology, calcium phosphate precipitation, direct microinjection, viral vector delivery, and the like. The choice of method is generally dependent on the type of cell being transformed and the circumstances under which the transformation is taking place (i.e. in vitro, ex vivo, or in vivo). A general discussion of these methods can be found in, e.g., Brent et al, supra.

Alternatively, where the host cell or cells are part of a multicellular organism, the targeting vector may be administered to the organism or host in a manner such that the targeting vector is able to enter the host cell(s), e.g., via an in vivo or ex vivo protocol. By "in vivo," it is meant in the target construct is administered to a living body of an animal. By "ex vivo" it is meant that cells or organs are modified outside of the body. Such cells or organs are typically returned to a living body. Methods for the administration of nucleic acid constructs are well known in the art. For example, nucleic acid constructs can be delivered with cationic lipids (Goddard, et al, Gene Therapy, 4:1231-1236, 1997; Gorman et al., Gene Therapy 4:983-992, 1997; Chadwick et al., Gene Therapy 4:937-942, 1997; Gokhale et al., Gene Therapy 4:1289-1299, 1997; Gao and Huang, Gene Therapy 2:710-722, 1995), using viral vectors (Monahan et al., Gene Therapy 4:40-49, 1997; Onodera et al., Blood 91:30-36, 1998), by uptake of "naked DNA", and the like. Techniques well known in the art for the transfection of cells (see discussion above) can be used for the ex vivo administration of nucleic acid constructs. The exact formulation, route of administration and dosage can be chosen empirically. See e.g. Fingl et al., 1975, in *The Pharmacological Basis of Therapeutics*, Ch. 1 p 1).

VI. Evolving rRNA for Enhanced Translation Efficiency or Altered Ribosome Function The polynucleotides encoding the synthetic mammalian 18S rRNA or related expression vector described herein are useful for identifying mutations (e.g., in 18s rDNA sequence) that cause improved or altered ribosomal functions and translation activities. The 18S rRNA expression system described herein can also be used for functional analysis of natural variations in 18S rRNA. They are also suitable for evolving rRNA sequences to produce ribosomes with improved properties, e.g., enhanced translation efficiency. For example, to increase expression of a specific polypeptide of interest, specific mutations can be introduced in 18S rRNA for enhanced base pairing interactions between rRNA and mRNA encoding the polypeptide of interest. By shutting down endogenous 18S rRNA function, the pactamycin-resistant 18S rRNA expression system described herein allows one to screen and select for mutations in 18S rRNA that would increase expression of a protein of interest. Similarly, rRNA sequences especially 18S rRNA can be evolved and selected for modified sequences which lead to ribosomes with altered assembly or enhanced translation activities not limited to any specific mRNA (e.g., interactions with tRNA).

Accordingly, provided are methods for studying functional consequences of mutations or natural variations in 18S RNA sequence. In some embodiments, effect of natural variations in an 18S rRNA sequence is examined via the use of the expression system described herein. Typically, a polynucleotide sequence bearing natural variations (e.g., mouse or human variant 18S rRNA sequence described herein) is modified to introduce pactamycin resistance as disclosed herein, e.g., introducing a substitution corresponding to G963A in SEQ ID NO:23. The modified polynucleotide present in an expression vector is then introduced into a host cell for functional analysis of rRNA processing and ribosome function in the presence of pactamycin. Any difference in the examined activities relative to that of a wildtype or reference 18S rRNA sequence (e.g., SEQ ID NO:23) would indicate a structure-function relationship between the sequence variation and the observed alteration in rRNA processing and/or ribosome activities.

In some other embodiments, the 18S rRNA expression system is employed to screen for mutations in the 18S rRNA sequence that cause altered ribosome functions and/or translation activities. In these embodiments, a polynucleotide sequence encoding a pactamycin-resistant mammalian 18S rRNA sequence or fragment thereof is further modified to generate candidate 18S rDNA sequences via random or site-specific mutagenesis. Upon introducing into a host cell, the candidate or variant 18S rDNA sequences are then subject to screening and selection to identify mutations that confer enhanced translation efficiency or altered ribosomal functions. The mutagenesis and subsequent selection can be performed using standard molecular biological techniques described herein.

Still some other embodiments described herein are directed to evolving an 18S rRNA sequence for enhanced expression of a specific polypeptide of interest. In these embodiments, random or site-specific mutations are introduced into the polynucleotide sequence encoding the pactamycin-resistant 18S rRNA provided that the mutations do not affect the pactamycin resistance activity of the encoded 18S rRNA. Random mutations of the rRNA-encoding sequence may be generated using methods well known in the art. For example, DNA shuffling as described in Stemmer, (Nature 370:389-391, 1994) can be readily employed to introduce random mutagenesis in the rDNA sequence. Alternatively, error prone amplification may be used to introduce random mutations, e.g., as described in Bartell and Szostak, Science 261:1411, 1993. Additional techniques for generating random mutations can also be used. For example, the 18S rRNA encoding sequence may also be mutated by cassette mutagenesis (Hutchison et al., Methods Enzymol. 202:356-390, 1991), recursive ensemble mutagenesis (Arkin et al., Proc. Natl. Acad. Sci. USA 89:7811-7815, 1992), exponential ensemble mutagenesis (Delegrave et al., Biotechnol. Res. 11:1548-1552, 1993), and sexual PCR mutagenesis (Stemmer et al., Proc. Natl. Acad. Sci. USA 91:10747-10751, 1994).

Other than random mutagenesis, candidate 18S rDNA sequence variants to be selected and screened for enhanced translation activities or altered ribosome functions can also be generated via targeted or site-specific mutagenesis. Site-directed mutagenesis in the 18S rDNA sequence can be performed with methods well known in the art, e.g., Arnold Curr. Opinion Biotechnol 4:450-455, 1993. In some embodiments, the 18S rDNA sequence variants are created using oligonucleotide directed mutagenesis to generate site-specific mutations. Oligonucleotide mutagenesis is described, e.g., in Reidhaar-Olson, Science 241:53-57, 1988. Briefly, a plurality of double stranded oligonucleotides bearing one or more mutations to be introduced into the cloned DNA are synthesized and inserted into the cloned DNA to be mutagenized. Clones containing the mutagenized DNA are recovered and the activities of the rRNAs they encode are then assessed. Another method for generating variant 18S rDNA sequences is via assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

For screening and selection for mutations with desired phenotypes, the variant 18S rDNA sequences which encode the pactamycin-resistant 18S rRNA and further bear a site-specific mutation or random mutations are then introduced into a host cell via an expression vector described herein. This is followed by culturing the cells in the presence of pactamycin and assessing expression level of a polypeptide of interest or other translation activity of the assembled ribosomes. For identifying modified 18S rRNA for enhanced expression of a specific polypeptide, expression level of that specific polypeptide in the cells is examined and compared to expression level of the same polypeptide in control cells which express the pactamycin-resistant 18S rRNA but do not contain other mutations in the 18S rRNA. A mutation in the 18 S rRNA which leads to enhanced translation level of the polypeptide of interest relative to that without the mutation indicates that the host cell has produced ribosomes with enhanced expression of the polypeptide of interest. As detailed below, the methods described herein are suitable for enhancing expression levels of various polypeptides or proteins of interest. The polypeptides of interest can be either endogenous or exogenous to the host cell.

Other than selecting for modified 18S rRNA sequence which confers enhanced expression level of a polypeptide of interest, the 18S rRNA expression system described herein can also be used to produce ribosomes with other altered functions. In these embodiments, the polynucleotides which encode the pactamycin-resistant 18S rRNA and further bear a site-specific mutation or random mutations described above can be examined in a host cell for any altered ribosomal activities arising from the mutations. The ribosomal activities that can be monitored include, e.g., ribosome assembly, interactions with tRNA and/or mRNA, translation initiation, and elongation and termination. The various ribosome functions can be monitored with techniques or assays that are routinely practiced in the art. For example, rRNA maturation and ribosome assembly for mammalian cells can be examined with the techniques described in, e.g., Pestov et al., Curr. Protoc. Cell Biol. 2008, Chapter 22:Unit 22.11; Champney, Methods Mol. Med. 142:63-73, 2008; and Klostermeier et al., Nucleic Acids Res. 32:2707-15, 2004. Ribosome binding to mRNA can be studied with assays that are similar to that described in, e.g., Day et al., J. Bacteriol. 186:6864-6875, 2004. Ribosome binding to ER membrane during protein translocation may be monitored with assays described in, e.g., Prinz et al., EMBO J. 19:1900-1906, 2000; and Kalies et al., J. Cell Biol. 126: 925-934, 1994. Binding of aminoacyl-tRNA to ribosome can be examined in accordance with standard binding assays well known in the art, e.g., Agafonov et al., EMBO Rep. 2:399-402, 2001; Ashraf et al., RNA. 5:188-194, 1999, and Lill et al., Methods Enzymol. 164:597-611, 1988. Potential effect of an 18S rRNA mutation on other aspects of protein synthesis (e.g., translation initiation, elongation, termination and peptide release) can also be monitored with routinely practiced assays. See, e.g., Burakovsky et al., RNA. 16:1848-53, 2010; Sternberg et al., Nat. Struct. Mol. Biol. 16:861-8, 2009; Van Dyke et al., Nucleic Acids Res. 37:6116-25, 2009; Sunohara et al., J. Biol. Chem. 279:15368-75, 2004; Khan et al., Biochim. Biophys. Acta. 1779:622-7, 2008; Anderson et al., J. Biol. Chem. 282:14752-60, 2007; Merill et al., J. Virol. 80:6936-42, 2006; Brunelle et al., RNA. 14:1526-31, 2008; Rawat et al., J. Mol. Biol. 357:1144-53, 2006; and Gong et al., J. Bacteriol. 189:3147-55, 2007.

VII. Polypeptides or Proteins of Interest for Enhanced Translation

The expression vectors and host cells expressing pactamycin-resistant 18S rRNA are useful for enhancing expression levels of important polypeptides or proteins of interest. The proteins of interest can be any polypeptides with medical or industrial applications. In some embodiments, the polypeptide or protein of interest is one that encodes a therapeutic protein. Examples of therapeutic proteins include factor VIII, factor IX, β-globin, low-density lipoprotein receptor, adenosine deaminase, purine nucleoside phosphorylase, sphingomyelinase, glucocerebrosidase, cystic fibrosis transmembrane conductance regulator, α-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, interleukins, cytokines, small peptides, and the like. Other therapeutic proteins that can be expressed from an intergrated target polynucleotide in the engineered host cell as described herein include, e.g., Herceptin®, polypeptide antigens from various pathogens such as disease causing bacteria or viruses (e.g., *E. coli, P. aeruginosa, S. aureus*, malaria, HIV, rabies virus, HBV, and cytomegalovirus), and other proteins such as lactoferrin, thioredoxin and beta-caseinvaccines.

Additional examples of proteins of interest include, but are not necessarily limited to insulin, erythropoietin, tissue plasminogen activator (tPA), urokinase, streptokinase, neutropoesis stimulating protein (also known as filgastim or granulocyte colony stimulating factor (G-CSF)), thrombopoietin (TPO), growth hormone, emoglobin, insulinotropin, imiglucerase, sarbramostim, endothelian, soluble CD4, and antibodies and/or antigen-binding fragments (e.g, FAbs) thereof (e.g., orthoclone OKT-e (anti-CD3), GPIIb/IIa monoclonal antibody), liary neurite transforming factor (CNTF), granulocyte macrophage colony stimulating factor (GM-CSF), brain-derived neurite factor (BDNF), parathyroid hormone (PTH)-like hormone, insulinotrophic hormone, insulin-like growth factor-1 (IGF-1), platelet-derived growth factor (PDGF), epidermal growth factor (EGF), acidic fibroblast growth factor, basic fibroblast growth factor, transforming growth factor β, neurite growth factor (NGF), interferons (IFN) (e.g., IFN-α2b, IFN-α2a, IFN-αN1, IFN-β1b, IFN-γ), interleukins (e.g, IL-1, IL-2, IL-8), tumor necrosis factor (TNF) (e.g, TNF-α, TNF-β), transforming growth factor-α and -β, catalase, calcitonin, arginase, phenylalanine ammonia lyase, L-asparaginase, pepsin, uricase, trypsin, chymotrypsin, elastase, carboxypeptidase, lactase, sucrase, intrinsic factor, vasoactive intestinal peptide (VIP), calcitonin, Ob gene product, cholecystokinin (CCK), serotonin, and glucagon.

Suitable polypeptides of interest also include specific membrane proteins or other intracellular proteins. Examples of membrane proteins include, but are not necessarily limited to adrenergic receptors, serotonin receptors, low-density lipoprotein receptor, CD-18, sarcoglycans (which are deficient in muscular dystrophy), etc. Useful intracellular proteins include proteins that are primarily located within the intracellular compartment or which exhibit a desired biological activity within a cell. Such intracellular proteins can include fumarylacetoacetate hydrolase (FAH) which is deficient in subjects with hereditary tyrosinemia Type 1. Other specific examples of intracellular proteins include antiviral proteins (e.g., proteins that can provide for inhibition of viral replication or selective killing of infected cells), structural protein such as collagens, i.e. the type VII collagen COL7A1 gene, defective in Recessive Dystrophic Epidermolysis Bullosa (RDEB) and dystrophin, defective in muscular dystrophy.

EXAMPLES

The following examples are provided for further illustration, but not to limit the scope. Other variants will be readily apparent to one of ordinary skill in the art and are encompassed by the appended claims.

Example 1

Identification of an Abundant 18S rRNA Variant

Mammalian cells contain several hundred rDNA genes that are not identical. These sequence variants provide a source of ribosomal heterogeneity and may have functional consequences. Several sequences were cloned from mouse N2a genomic DNA. rDNA fragments were PCR-amplified using primers rDNA.1 and rDNA.2 (Table 1), located ≈700 nucleotides upstream and 70 nucleotides downstream of the 18S rDNA, respectively. Six independent clones were sequenced and found to be >99% identical to each other. However, none of these sequences are completely identical to each other or to two different 18S rDNA sequences in the NCBI nucleotide database (X82564, NR_003278, X00686; sequences X82564 and NR_003278 contain identical 18S sequences). In addition to several unique variations that differ from the published sequences, the sequences identified in this study share a nucleotide difference in helix H41a and two single nucleotide insertions, one in expansion segment 3 and the other in helix H30.

TABLE 1

Oligonucleotide primer and probe sequences.

| Oligo name | Sequence (SEQ ID NO:) |
|---|---|
| rDNA.1 | 5'-GACGTTGCGCCTCGCTGCTG-3' (1) |
| rDNA.2 | 5'-CGCCTCCCGGCGAGGACACA-3' (2) |
| rDNA.3 | 5'-NNNAGATCTGGGTCGACCAGTTGTTCC-3' (3) |
| rDNA.4 | 5'-CAAGTAGGAGAGGAGCGAGC-3' (4) |
| rDNA.5 | 5'-GGTGTCTTGCGCGGTCTTGG-3' (5) |
| rDNA.6 | 5'-CGCTGAGAAGACGGTCGAAC-3' (6) |
| rDNA.7 | 5'-GATCGATGCGGCCGCGTATCGGTATTTCGGGTGTG-3' (7) |
| rDNA.8 | 5'-CAAGCTTCTGCAGG-3' (8) |
| rDNA.9 | 5'-CTAGCCTGCAGAAGCTTGAGCT-3' (9) |
| rDNA.10 | 5'-TAATACGACTCACTATAGGG\|TACCTGGTTGATCCTGCCAGTAGC-3' (10) |
| rDNA.11 | 5'-TAATGATCCTTCCGCAGGTTCACC-3' (11) |
| rDNA.12 | 5'-NNNGCTAGCGTACTGACACGCTGTCCTTTCCC-3' (12) |
| 24-nt hybridization tag | 5'-AGGCCCATCTCTGCTAGGAGAGCT-3' (13) |
| α-tag probe | 5'-CTCCTAGCAGAGATGGGCCTAGCT-3' (14) |
| α-5' ETS probe | 5'-GAGAGCGCGAGAGAGGAG-3' (15) |
| α-ITS1 probe | 5'-ACACACAAGACGGGGAGA-3' (16) |
| α-18S rRNA probe | 5'-GCCCCGCGGGACACTCA-3' (17) |
| 693RT | 5'-GTCTTGCGCCGGTCCAAGAA-3' (18) |

TABLE 1-continued

Oligonucleotide primer and probe sequences.

| Oligo name | Sequence (SEQ ID NO:) |
|---|---|
| Pol-I.1 | 5'-NNNAGATCTGGGTCGACCAGTTGTTCC-3' (19) |
| Pol-I.2 | 5'-NNNGCTAGCTACCTATCTCCAGGTCCAATAGG-3' (20) |
| Pol-I.3 | 5'-NNNGCGGCCGCGTGGGATCCCCATCCTCG-3' (21) |
| Pol-I.4 | 5'-NNNCAATTGCGACCACCAGACTTTCTGAC-3' (22) |

For the expression system, an 18S rDNA gene sequence that contains the most common sequence variants at each nucleotide position was used to provide a reference for future studies of rRNA sequences that contain less common sequence variants. To assess how the cloned sequences compare to the population of 18S rDNA sequences, they were compared to sequences obtained using pooled genomic PCR products as templates. Barring significant bias in the PCR reactions, the sequences of the pooled genomic sequences should represent the major genomic variants at each nucleotide. Two independent PCR reactions (PCR1 and PCR2) were performed and the products sequenced directly. Comparison of the pooled genomic sequence to those of the clones isolated in this study revealed that one of the clones contains the same sequence as the pooled genomic sequence. This clone (accession No. JQ247698; SEQ ID NO. 23) was selected for subsequent experiments. It is 1,871 nucleotides long and contains the 3 shared mutations discussed above, but no other variations from published sequence X00686.1 (SEQ ID NO: 34).

Example 2

Development of an 18S rRNA Expression Construct

An 18S rRNA expression system was developed in order to study the role of this RNA in the biogenesis of 40S ribosomal subunits, and in the process of translation initiation. It was expected that mouse rDNA genomic fragments may need the A', $A_0$, 1, and 2 sites for proper processing (FIG. 1b). The 18S rDNA clone identified above was used to generate expression constructs containing the 5' ETS, 18S rDNA, and ITS1, which include all of these sites (FIG. 2a). Constructs were generated using the pol-I promoter and 3' ETS, or the cytomegalovirus (CMV) promoter and an SV40 poly(A) signal. Also tested were constructs with deletions at the 5' end of the 5' ETS and the 3' end of ITS1, i.e. with less authentic spacer sequence flanking the processed (mature) ends of the 18S rRNA. These various constructs were transfected into N2a cells and expression of synthetic 18S rRNAs was determined by Northern blotting with an oligonucleotide probe to a 24 nt hybridization tag that was cloned into expansion segment 3 of the 18S rDNA. The results revealed that only constructs with the full-length 5' ETS, containing sites A' and $A_0$, yielded a band corresponding to properly processed 18S rRNA (p18S.1 and 18S.2 (Pol-1 and CMV); FIG. 2b) confirmed by size comparison to an in vitro 18S RNA transcript. By contrast, ITS1, which contains 3' processing sites 2b and 2c, does not appear to be required, as construct p18S.2(Pol-1 and CMV) generates a band corresponding to mature 18S rRNA even though the majority of ITS1 is deleted in this construct.

Expression of mature 18S rRNA was observed to occur with both pol-I and CMV promoters; however, the levels were much higher when transcription was mediated by pol-I (FIG. 2b). The results indicate that the processing sites in the 5' ETS are sufficient for processing of 18S rRNA, and that processing does not require transcription to occur from RNA polymerase I. Due to the low yield observed with pol-II transcription of 18S rRNA, the pol-I vector was used exclusively for all subsequent experiments.

Figure 7:
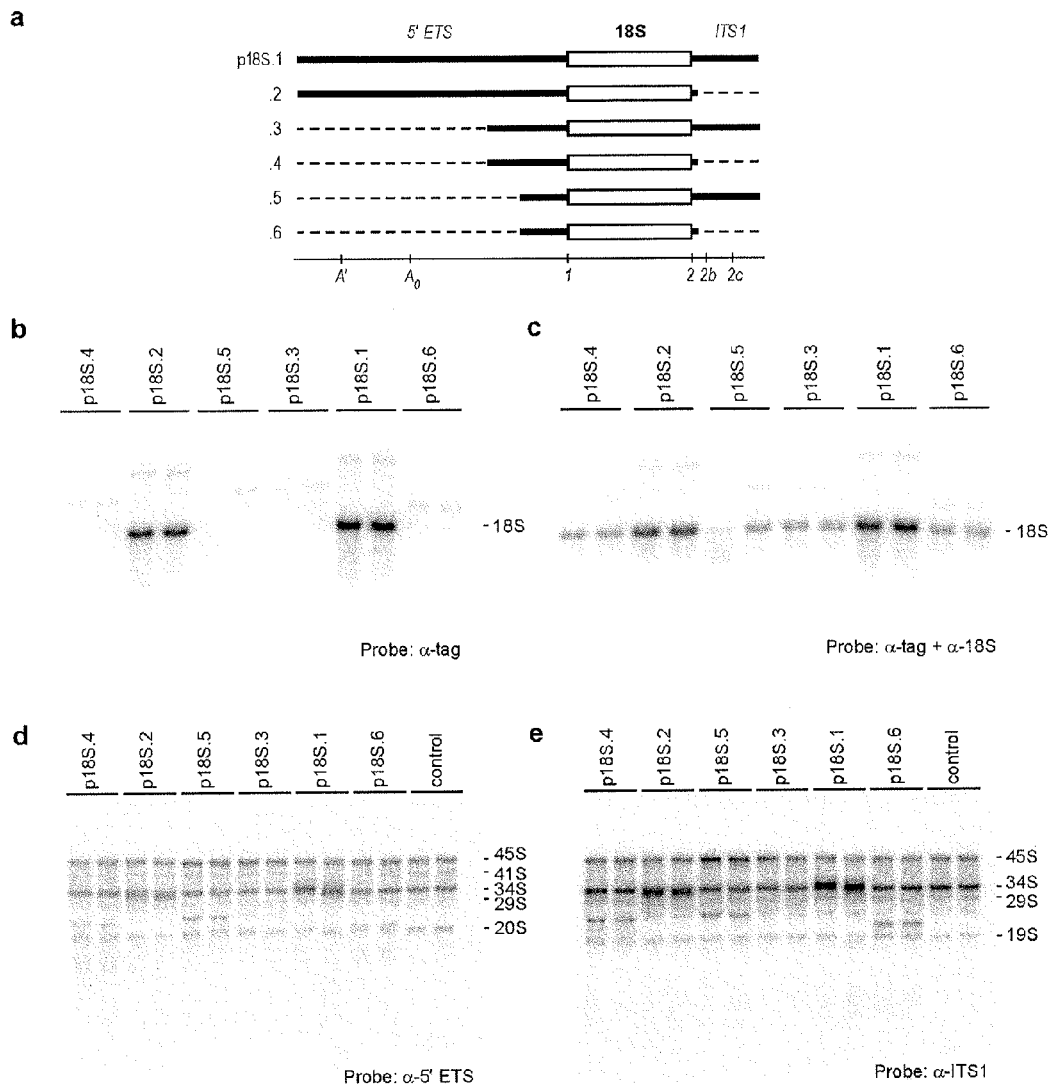
FIGS. 7a-7e show analysis of 18S rRNA maturation. (a) Schematic representation of constructs. Constructs contain a pol-I promoter and 3' ETS. Northern blots in panels b-e contain RNA from N2a cells transfected with various 18S rRNA constructs and from untransfected (control) cells as indicated. (b) Northern blot analysis of synthetic 18S rRNAs using the α-tag probe. (c) Northern blot from panel b was re-probed with α-18S rRNA probe to detect endogenous 18S rRNAs in the same samples. (d) Northern blot analysis of 5' ETS-containing pre-rRNAs using α-5' ETS probe which hybridizes to sequences located immediately 5' of site 1. (e) Northern blot analysis of ITS1-containing pre-rRNAs using α-ITS1 probe which hybridizes to sequences located immediately 3' of site 2. Sizes in panels d and e are indicated for known pre-rRNAs, corresponding to those shown in FIG. 1.

Correct processing of the synthetic 18S rRNA precursor transcripts from constructs p18S.1 and p18S.2 was shown by probing blots with the α-tag probe to identify these 18S rRNAs. The same blots were re-probed with a low specific activity oligonucleotide probe (α-18S) that recognizes both synthetic and endogenous 18S rRNAs (FIGS. 7a,b,c). The results show that the mature synthetic and endogenous 18S bands are superimposable. To demonstrate removal of spacer regions from processed RNAs, Northern blots were performed with probes complementary to sequences in the 5' ETS (α-5' ETS) and ITS1 (α-ITS1), located immediately 5' and 3' of sites 1 and 2, respectively (FIGS. 7d,e). Both blots showed no detectable hybridization with the mature tagged transcript, but hybridized to the longer low abundance precursor transcripts, results consistent with the removal of spacer regions from the mature 18S rRNA. For constructs with deletions in the spacer regions, sizes of the unprocessed and partially processed transcripts are consistent with those expected when compared to pre-rRNA species.

To monitor the relative levels of the synthetic 18S rRNA following transfection, time course experiments were performed. For these experiments the full-length pol-I construct (p18S.1) that yielded processed 18S rRNA was transfected into cells, and 18S rRNA expression was monitored by harvesting cells at various time points up to 72 h post-transfection and then probing for the hybridization tag (FIG. 2c). For this construct, maximal expression of the synthetic 18S rRNA, as a percentage of total 18S rRNA, was observed 36-48 hours post transfection. All subsequent experiments were performed 48 hours post-transfection unless otherwise noted.

Figure 8:
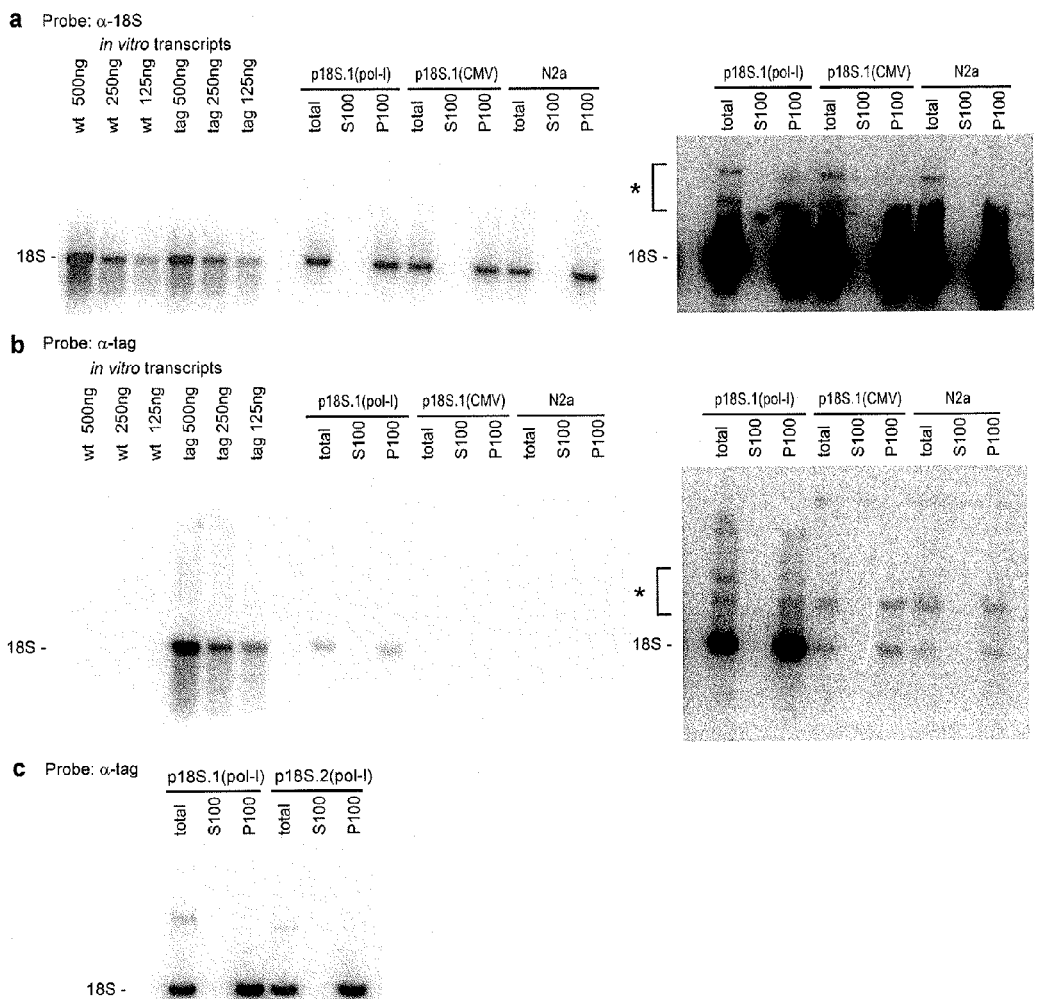
FIG. 8a-8c show sedimentation analysis of synthetic rRNA species. (a) Northern blot analysis of total RNA (total) and RNA from cellular fractionation through centrifugation into S100 and P100 fractions. RNA was from cells that were either untransfected (N2a) or transfected with p18S.1(pol-1) or p18S.1(CMV) constructs as indicated. In vitro transcripts of wild-type 18S rRNA (wt) and 18S rRNA containing the hybridization tag (tag) were electrophoresed alongside as hybridization and size controls. The blot was hybridized using the α-18S rRNA probe. The image to the right shows part of the image to the left that was contrast adjusted to reveal bands, indicated by an asterisk, that correspond to full-length and partially processed transcripts. (b) This blot was hybridized using the α-tag probe. The image to the right corresponds to part of the image to the left that was contrast adjusted. Background hybridization of endogenous rRNAs with the α-tag probe is seen in the N2a samples. (c) Cells were transfected with either p18S.1(pol-I) which contains ITS1 or p18S.2(pol-I) which lacks ITS1 as indicated. This blot was hybridized using the α-tag probe.

To determine whether the processed synthetic 18S rRNAs are associated with ribosomes, Northern blot analyses were performed of whole cell lysates and of pellet and supernatant fractions of lysates of cells transfected with p18S.1 prepared by centrifugation at 100,000×g (FIGS. 8a,b). As seen earlier, both unprocessed and processed synthetic 18S rRNAs were present in total RNA prepared from whole cell lysates (FIGS. 8a,b; right images). However, in the fractionated material, only processed rRNA was seen in the P100 pellet, which contains sedimented ribosomes. Processed RNA was not seen in the supernatant fraction, which contains less dense cytoplasmic material. These fractionated RNA samples were also compared to synthetic in vitro transcribed rRNAs by probing with both α-tag and α-18S probes for determination of relative abundance. Synthetic 18S rRNA in cells 48 hours post-transfection was estimated to be ≈10-15% of total 18S rRNA. Fractionation of lysates from cells transfected with p18S.2

(pol-I) yielded similar results (FIG. 8c), suggesting that synthetic 18S rRNAs lacking ITS1 are incorporated into ribosomal subunits. Taken together, these experiments indicate that the synthetic 18S rRNAs derived from p18S.1 and p18S.2 were correctly processed and incorporated into 40S subunits. They also show that ITS1 is dispensable for formation of mature 18S rRNA.

Example 3

Analysis of 5' ETS Sequences

The 5' region of the 5' ETS containing the A' and $A_0$ processing sites appears to be required for processing of 18S rRNA (FIG. 1b); however, little is known about the importance of sequences located 3' of these sites in mammalian rDNA genes. The length of these 3' sequences in mammalian genes differentiates them from other eukaryotic rDNA genes, which are substantially shorter. To investigate the potential contribution of these additional sequences in mammals, several internal deletions were generated, including deletions to remove the A' and $A_0$ sites, individually and in combination (FIG. 3a).

Northern blots of RNA extracted from cells transfected with the internal deletion constructs were hybridized using an oligonucleotide probe to the hybridization tag. The results confirmed that deletions that remove the A' or $A_0$ cleavage sites block processing (p18S.9, .10, and .11; FIG. 3b); however, deletion of the expanded 3' region of the 5' ETS had little to no effect on the maturation of 18S rRNA (p18S.7). This result suggests that this region lacks important cleavage sites and other points of interaction with rRNA processing factors.

Cleavage at A', $A_0$, and site 1 requires the U3 snoRNA and in mouse, putative binding sites for the U3 snoRNA have been postulated based on complementary sequence matches to two regions in the snoRNA, termed the 3' and 5' hinge regions. Based on these predictions and observations, deletions in p18S.9, .10 and .11 removed several potential binding sites for the U3 snoRNA 3' hinge at nucleotides 667-673, 1032-1038 and 1117-1123, while deletions in p18S.8, p18S.9 and p18S.10 removed a potential binding site for the 5' hinge at nucleotides 1552-1560. In all of these constructs, the deletions blocked processing. The deletion in p18S.8 removes a 9-nt putative binding site for the 5' hinge of the U3 snoRNA, but still contains both the A' and $A_0$ cleavage sites. To specifically test the requirement of this putative binding site for processing, the 9-nt sequence in the 5' ETS in constructs p18S.8Δ and p18S.8m, respectively (FIG. 3c) were deleted or mutated. Northern blot analysis of RNA from cells transfected with these constructs shows that disruption of the 9-nt sequence in both constructs almost completely abolished processing. This result supports that this 9-nt sequence binds to the U3 snoRNA 5' hinge region.

As A' cleavage is dependent on U3 snoRNA, it is notable that removal of the putative 5' hinge region in constructs p18S.8 and p18S.9 results in multiple immature rRNA bands, indicating incomplete cleavage at A' (FIG. 3b). It appears that some A' cleavage can still occur without sequences complementary to the U3 snoRNA 5' hinge. In contrast, p18S.11, which lacks the A' site and a potential 3' hinge binding site, and p18S.10, which lacks binding sites for both hinge regions, yields an uncleaved primary transcript, indicating no discernible cleavage at $A_0$ in the absence of A', the 3' hinge region, or a combination of these sites.

Example 4

Identification of Pactamycin Resistance Mutations and Verification of Subunit Function The ability to selectively monitor translation from subunits containing synthetic 18S rRNAs in vivo requires being able to shut down endogenous subunits in order to differentiate between the activities of modified and endogenous ribosomal subunits (FIG. 1a). This approach is necessary, as quantification of Northern blots of the types shown in FIG. 9 suggested that ribosomal subunits containing synthetic rRNA only represent a small portion (up to ≈10-15%) of total cellular 40S ribosomal subunits ≈48 hours post transfection.

Figure 4:
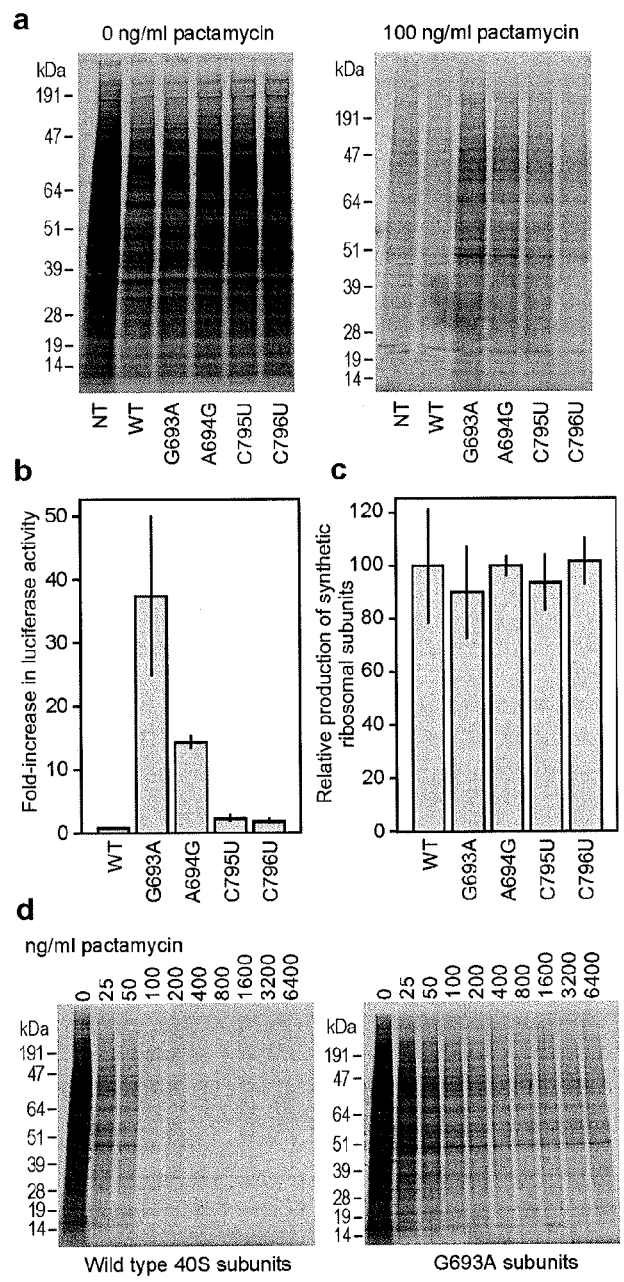
FIGS. 4a-4d show analysis of pactamycin-resistance mutations in N2a cells. (a) Protein expression in cells expressing wild-type or mutated 18S rRNA constructs. Cells were either not transfected (NT) or transfected with constructs expressing wild type (WT) 18S rRNA or 18S rRNAs containing the point mutations indicated. Cells were then $^{35}S$ pulse-labeled in the absence or presence of 100 ng/ml pactamycin as indicated, cells were lysed, and equal volumes of the cell lysates were analyzed by SDS-PAGE, as described in Methods. Representative autoradiograms are shown. (b) Relative luciferase activities in cell lysates from cells transfected with wild-type or mutated 18S rRNAs and with pGL4.13 (Promega). N2a cells were cotransfected with the 18S rRNA constructs indicated and with a firefly luciferase construct (pGL4.13) and luciferase expression monitored from cell lysates. Luciferase activities are relative to those obtained from cells transfected with the WT construct, which is set to 1.0. Details of the cotransfection and assay methods are described in Example 7. (c) Quantification of synthetic rRNA levels from Northern blots for cells transfected with WT or mutated rRNA constructs. Synthetic rRNA was detected by hybridization with the α-tag probe. Signals were quantified using a Molecular Dynamics Phosphorimager and are represented relative to WT, with WT set to 100%. (d) Cells were transfected with either wild-type or G693A mutation-containing 18S rRNA constructs and incubated with various amounts of pactamycin as indicated. Cells were $^{35}$S pulse-labeled, and cell lysates analyzed by SDS-PAGE. Representative autoradiograms are shown. In panels (c) and (d) error bars represent standard deviations from 3 independent experiments.

There were no reports of functionally tested examples of nucleotide changes conferring antibiotic resistance in higher eukaryotes. Pactamycin affects translation by binding to rRNA in the E-site of the small subunit and disrupting the positioning of mRNA at this site. The result of pactamycin-binding is a block in elongation and the accumulation of di-peptides resulting from aborted initiation events. Analyzed were the effects of mutations in mouse 18S rRNA at four residues, G963, A964, C1065 and C1066 in SEQ ID NO:23. These residues correspond, respectively, to positions 693, 694, 795 and 796 at the E-site of *E. coli* 16S rRNA which were identified from crystal structures. Unless otherwise noted, the numbering of these sites in mammalian 18S rRNA sequences is based on that in *E. coli* 16S rRNA. Mutations were introduced into a construct expressing the untagged mouse 18S rRNA and containing the full-length 5' ETS and ITS1 spacer regions (p18S.1(Pol-1)). Pactamycin resistance was assessed by 35S-Met/Cys pulse labeling of transfected cells in the presence of 100 ng/ml antibiotic. At each nucleotide position thought to interact with pactamycin, purine-purine (G693A, A694G) and pyrimidine-pyrimidine (C795U, C796U) transition mutations were generated. Cell lysates were compared from untransfected cells, cells expressing synthetic 18S rRNA, and synthetic mutated 18S rRNAs (FIG. 4a) by SDS-PAGE. Mutated ribosomes were also analyzed for their ability to translate a luciferase mRNA in cells transfected with a luciferase reporter plasmid (pGL4.13), and cultured in the presence of 100 ng/ml pactamycin (FIG. 4b). The results of both sets of experiments show that all four mutations confer some degree of pactamycin resistance. The G693A and A694G mutations showed the highest levels of resistance, while the C795U and C796U mutations gave results that were only slightly above background. The labeling results (FIG. 4a) suggest that none of the mutations significantly altered the protein banding pattern compared to wild-type ribosomes.

The G693A mutation, which conferred the highest level of pactamycin resistance, was used exclusively for further experiments. The levels of synthetic 18S rRNA for constructs with each mutation were monitored using the hybridization tag and found no substantial differences that could account for the difference in translation between G693A and the other mutations (FIG. 4c). To further characterize the G693A mutation, cells expressing wild type or mutated ribosomes were cultured with increasing concentrations of pactamycin. The results showed that translation from wild type 40S subunits was substantially blocked by 100 ng/ml pactamycin, but could be further blocked at higher concentrations. By contrast, translation from the mutated subunits appeared to be unaffected even at the highest concentration tested of 6,400 ng/ml (FIG. 4d).

Figure 5:
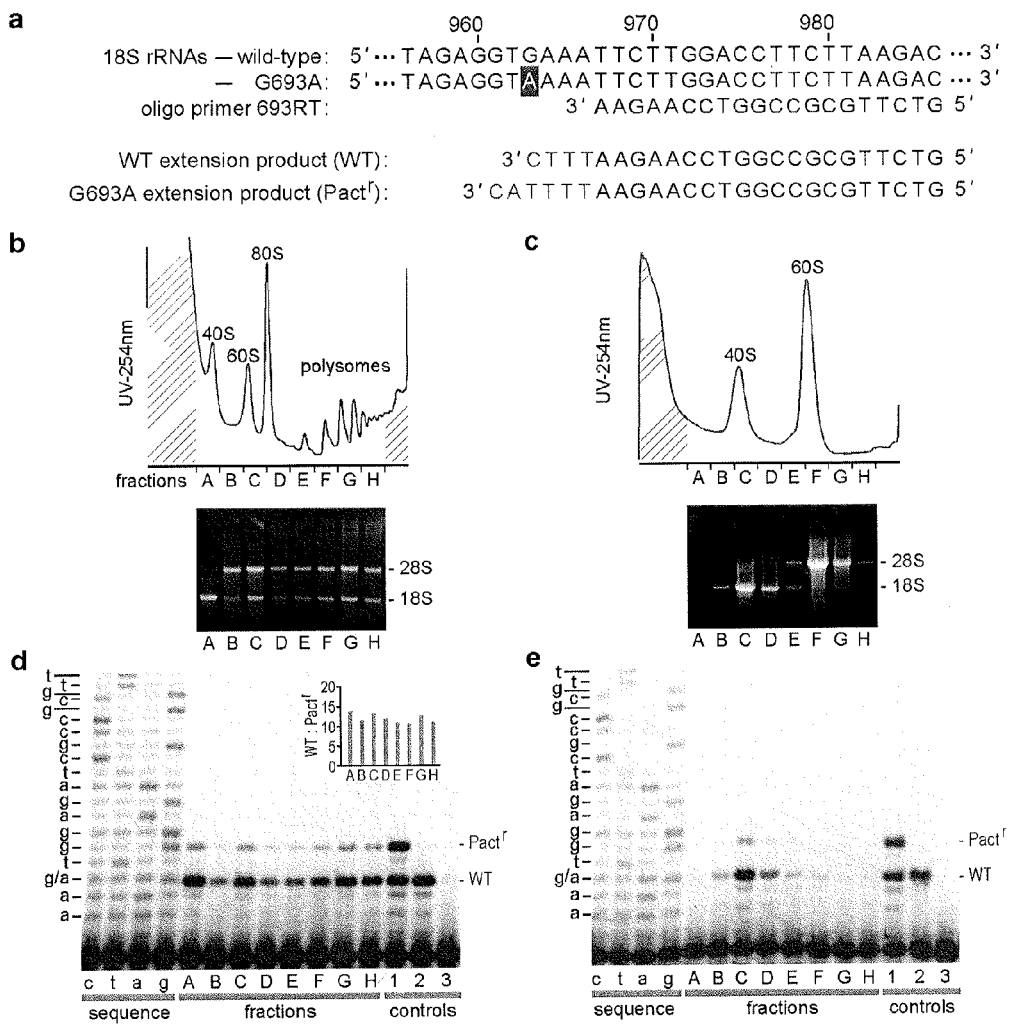
FIGS. 5a-5e show sucrose density gradient distributions of ribosomal subunits containing synthetic 18S rRNAs. (a) ddCTP primer extension assay. Partial sequences of wild type (SEQ ID NO:29) and mutated 18S rRNAs are shown. The position of the pactamycin-resistance mutation (G693A), located at nucleotide 963 in mouse 18S rRNA (SEQ ID NO:30), is highlighted. The sequence of oligonucleotide primer 693RT (SEQ ID NO:31) is shown aligned to its complementary match in the 18S rRNAs. Primer extension reactions performed in the presence of ddCTP will terminate at the first G located upstream of the primer. This will result in 4-nt-extended products from wild-type 18S rRNA templates (SEQ ID NO:32) and 6-nt-extended products from G693A-mutated 18S rRNAs (SEQ ID NO:33). In each case, the extended nucleotides are indicated at the 3' end. (b) Top: Lysates from cycloheximide-treated N2a cells transfected with p18S.1(G693A) were fractionated in a 10-50% (w/v) linear sucrose gradient. Peaks (left to right) represent 40S ribosomal subunits, 60S ribosomal subunits, 80S single ribosomes, and polysomes. The fractions (A-H) that were collected for RNA analysis are indicated. Bottom: RNA prepared from fractions A-H was visualized in an ethidium bromide-stained agarose gel. The 28S and 18S rRNAs are indicated. (c) Top: EDTA-dissociated ribosomes were fractionated on a 10-35% (w/v) linear sucrose gradient. Peaks (left to right) represent 40S and 60S ribosomal subunits. Bottom: RNA analysis as in panel (b). (d) PAGE analysis of RNA prepared from fractions of the sucrose gradient in panel b) which were subjected to ddCTP primer extension using oligonucleotide primer 693RT, which was $^{33}$-P-labeled. The sequencing reactions (lanes c,t,a,g) used the same primer with total RNA as a template. The upper bands are generated from the synthetic 18S rRNA (Pact$^r$) and the lower bands are from endogenous 18S rRNA (WT). Lanes 1-3 are controls. Control 1 is an equimolar mixture of in vitro transcripts that contain or lack the pactamycin resistance mutation. Control 2 is total RNA from untransfected N2a cells, which contains only the wild-type 18S rRNA. Control 3 is a no template control. The levels of the primer extension products from the various fractions were quantified from Phosphorimager exposures and the ratios of the two bands (WT:Pact$^r$) are shown in the inset. (e) ddCTP primer extension from fractions of gradient in panel (c).

Additional evidence of subunit function was obtained from sucrose density analysis of the distribution of ribosomes containing the G693A mutation. In these experiments, the distribution of ribosomal subunits containing wild type (endogenous) and synthetic (G693A) 18S rRNAs were compared by using an oligonucleotide primer (693RT) to hybridize downstream of the G693A mutation and ddCTP as a terminator (FIG. 5a). Under these reaction conditions, the mutated 18S rRNA generates a primer extension product that is two nucleotides larger than that generated from the endogenous rRNA. This primer extension reaction enables analysis of the presence and abundance of these rRNAs within the same sample. For these experiments, lysates were prepared from N2a cells transfected with the G693A construct and treated with either cycloheximide or EDTA. Lysates were then fractionated on sucrose density gradients (FIGS. 5b,c), and the resulting fractions analyzed by primer extension (FIGS. 5d,e). Analysis of the distribution of primer extension products through the cycloheximide profile (FIGS. 5b,d) showed the mutated rRNA has a relative distribution similar to that of the endogenous 18S rRNA through the polysomes. Quantification of WT and G693A primer extension products and comparison of their relative ratios shows a relatively equal distribution through the gradient (FIG. 5d inset), suggesting that ribosomal subunits containing synthetic 18S rRNA are functionally similar to those of endogenous subunits. Likewise, an EDTA-treated lysate confirms the presence of the mutated 18S rRNA in 40S subunits through its co-localization with the 40S peak (FIGS. 5c,e).

Example 5

Function of 40S Subunits from rRNA Precursors with Spacer Region Deletions

Figure 2:
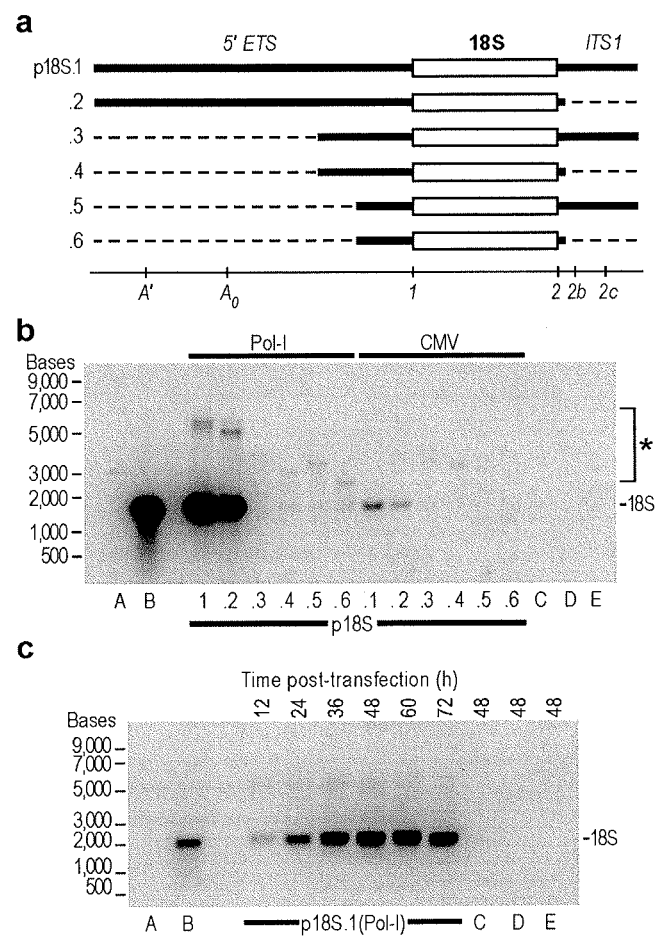
FIGS. 2a-2c show analysis of processing of rRNA constructs. (a) Schematic representation of RNAs expressed from constructs p18S.1-.6. Constructs contain either a pol-1 promoter and 3' ETS, or a CMV promoter and an SV40 poly(A) signal. The 5' ETS and ITS1 are indicated by thick black lines, the 18S rRNA by a yellow bar, and deleted spacer sequences by thin dashed lines. Cleavage sites are indicated. (b) Northern blot analysis of 18S rRNA processing. N2a cells were transfected with the constructs indicated and RNA analyzed by Northern blots as described in Methods. Nucleotide positions of a single stranded RNA size ladder are indicated to the left side of the blot. This blot contains the following controls: A: 100 ng 18S WT transcript, B: 100 ng 18S tagged transcript, C: 2 µg total RNA from N2a cells transfected with p18S.1 untagged (Pol-1), D: 2 µg total RNA from mock transfected N2a cells, E: 2 µg total RNA from N2a cells. Synthetic rRNA was detected by hybridization to an inserted tag sequence using the α-tag probe. The upper bands (asterisk) correspond to full-length and partially processed transcripts. The location of mature 18S rRNA is indicated. (c) Time course of 18S rRNA accumulation from construct p18S.1 (Pol-1). For these experiments N2a cells were transfected and RNA harvested at various times post-transfection as indicated. The controls are the same as in (b).
Figure 3:
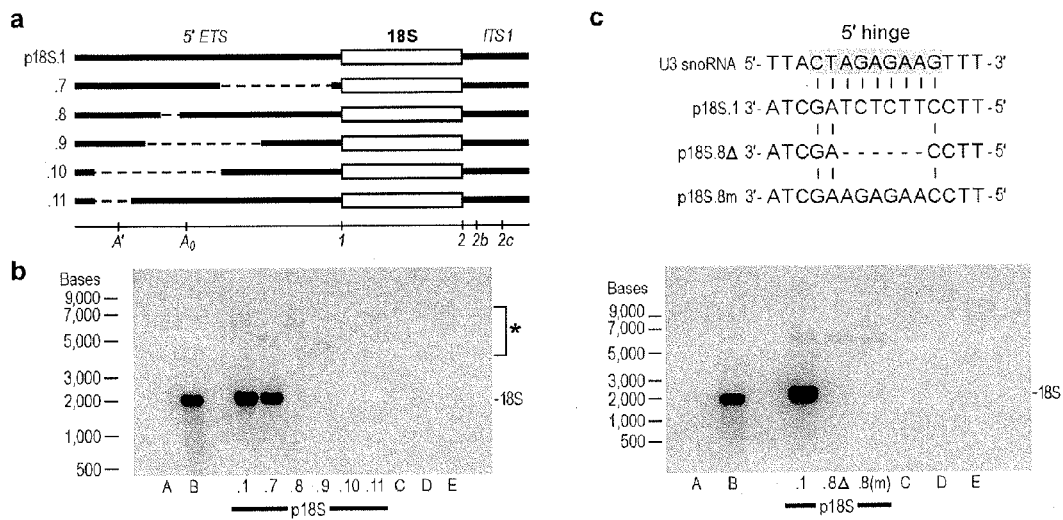
FIGS. 3a-3c show analysis of contribution of 5' ETS sequences to 18S rRNA processing. (a) Schematic representation of constructs as in FIG. 2. Constructs contain a pol-I promoter and 3' ETS. (b) Northern blot analysis of 18S rRNA processing. N2a cells were transfected with the constructs indicated and RNA analyzed by Northern blots as described in Methods. Synthetic rRNA was detected by hybridization to an inserted tag sequence using the α-tag probe. The asterisk indicates full-length and partially processed transcripts. The location of mature 18S rRNA is indicated. Controls for this blot are as described in FIG. 2. (c) Top: Schematic shows comparison of U3 snoRNA 5' hinge region (SEQ ID NO:25) to p18S.1 (SEQ ID NO:26), p18S.8Δ (SEQ ID NO:27), and p18S.8m (SEQ ID NO:28); the complementary sequence match to p18S.1 is highlighted. Bottom: The Northern blot shows synthetic rRNA expression from N2a cells transfected with the indicated constructs. This blot was hybridized with the α-tag probe, as in panel (b). Controls for this blot are as described in FIG. 2.

Several deletion constructs were identified which appear to yield properly processed, mature 18S rRNAs based on size (FIGS. 2 and 3). However, cleavage at the correct sites may not be sufficient to ensure that these rRNAs fold properly and incorporate into functional subunits because interactions between spacer regions and 18S rRNA may be necessary for correct folding. To determine whether rRNAs with deletions in the 5' ETS and ITS1 can adopt functional conformations in the context of 40S ribosomal subunits, the G693A mutation was introduced into constructs p18S.7 and .2, respectively, and tested them in cells co-transfected with either a monocistronic luciferase reporter construct (FIG. 6a), or a dicistronic dual luciferase vector (FIG. 6b), as described in Methods. Expression in each case was measured in the presence of pactamycin to inhibit translation from endogenous 40S subunits. It was expected that structural alterations resulting from erroneous ribosome formation or folding in the deletion constructs might differentially affect translation of these mRNAs, which represent cap-dependent translation and two classes of IRES-dependent translation that each requires various initiation factors for translation competence.

Figure 6:
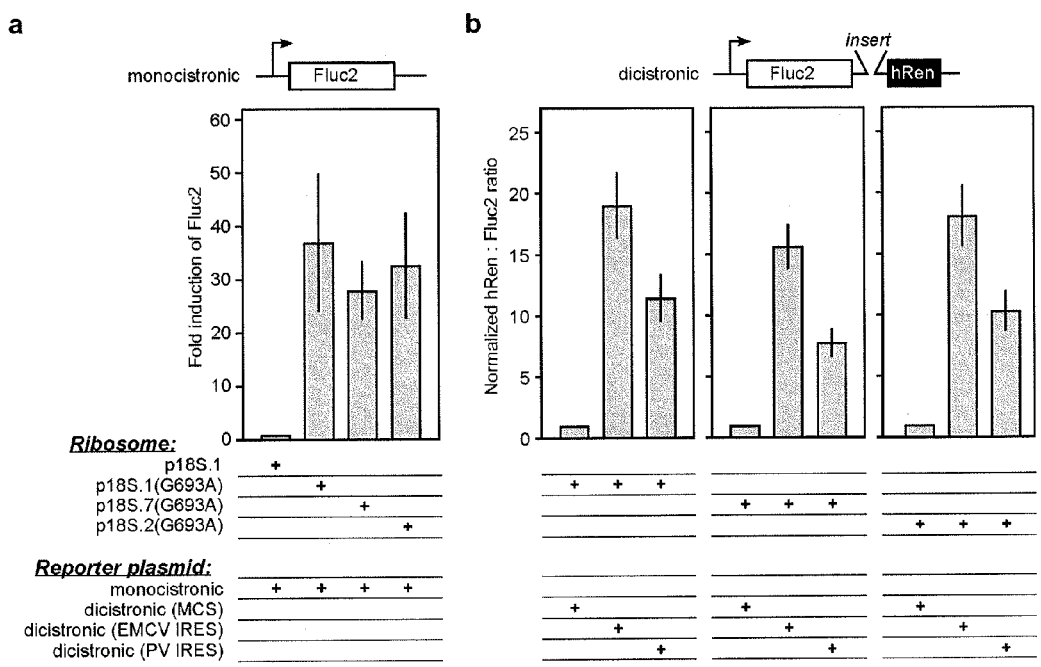
FIGS. 6a-6b show analysis of function of synthetic 18S rRNAs containing deletions in 5' ETS or ITS1. (a) Reporter assays of N2a cells cotransfected with a monocistronic reporter construct expressing an optimized firefly luciferase (Fluc2) and various 18S rRNA constructs as indicated. A schematic representation of the monocistronic construct is shown above. The synthetic rRNAs used in each experiment are indicated below the graph: p18S.1 contains the full 5' ETS and ITS1, p18S.7 contains a deletion of the 3' region of the 5' ETS, and p18S.2 lacks ITS1. Luciferase activities were determined as described in Methods. The results of the various transfections are reported as fold induction of Fluc2, which is luciferase activity over background obtained with wild-type (pactamycin-sensitive) ribosomes (p18S.1). (b) Reporter assays of N2a cells transfected with dicistronic reporter constructs expressing Fluc2 and an optimized human *Renilla* luciferase (hRen). The control construct contained a multiple cloning site (MCS) in the intercistronic region; the other constructs contained either the EMCV or PV IRES. The 18S rRNA constructs and reporter constructs used in each experiment are indicated below the graph. The results are reported as hRen to Fluc2 ratios normalized to the MCS construct, which has no IRES activity. Error bars represent standard deviations from 3 independent experiments.

For the monocistronic construct, no significant differences were observed between ribosomes, suggesting that the deletions in the spacer sequences did not disrupt assembly or affect the ability of the subunits to recruit the translation factors associated with cap dependent translation (FIG. 6a). For the dicistronic constructs, expression of the second cistron was measured, facilitated by either the EMCV or PV IRES in the intercistronic region, relative to a control sequence with no known IRES activity. The results showed that the ratio of expression of the two cistrons (hRen/luc2; FIG. 6b) was similar between the control and the spacer deletion rRNA constructs, suggesting that the ribosomal subunits in each case are indistinguishable from wild type in their abilities to translate mRNAs via these IRESes. These results further support the conclusion that ribosomal subunits derived from the shortened rRNA transcripts are active, and do not appear to require the sequences that were deleted from the 5' ETS and ITS1.

Example 6

Effects of 5' ETS and ITS1 on Overall Efficiency of Subunit Formation

Although deletions in the 5' ETS and ITS1 did not appear to affect the translation competence of 40S subunits, it was unclear if these flanking sequences might affect the efficiency of production of ribosomal subunits. Transfection conditions for the studies were optimized to maximize ribosomal subunit production, potentially masking differences in relative subunit abundance from each construct. Therefore experiments were performed to reduce expression of synthetic rRNA per cell by transfecting cells with diluted plasmid constructs. These experiments were performed using standard transfection conditions with the same amount of total plasmid per transfection; however, the amounts of the p18S rRNA expression plasmids (1 µg, 0.1 µg, and 0.01 µg) were varied by using another plasmid (pBS KS) as filler.

Figure 9:
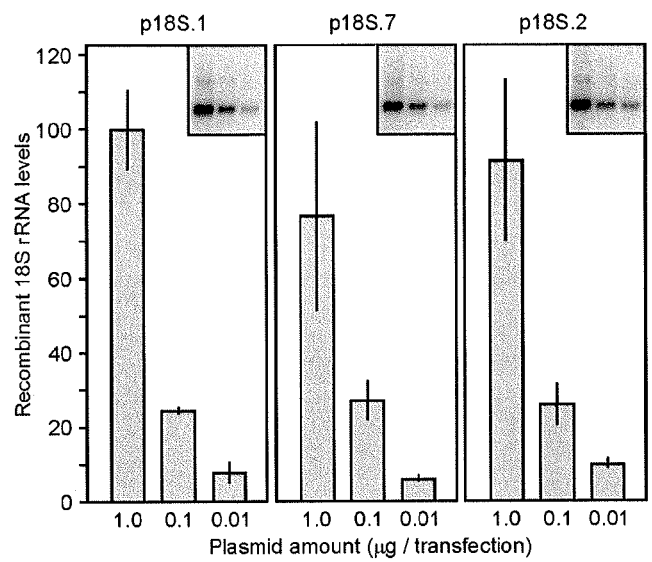
FIG. 9 shows analysis of mature 18S rRNA production from diluted plasmid transfections. Northern blot analysis of synthetic 18S rRNAs from cells transfected with different plasmid dilutions. Three vectors that form mature 40S subunits were tested: p18S.1 which contains the full-length 5' ETS and ITS1 sequences, p18S.7, which contains a deletion in the 5' ETS, and p18S.2, which contains a deletion in ITS1. The Northern blots were probed with the α-18S tag and the major band corresponds to mature 18S rRNA. Transfections were performed with pBS KS as a filler plasmid to retain transfection efficiency. Synthetic 18S rRNA levels are indicated on an arbitrary scale normalized to 100 for the p18S.1 construct at 1 µg plasmid/transfection.

The three expression constructs tested in this experiment contain the full-length 5' ETS and ITS1 sequences (p18S.1)), a deletion in the 5' ETS (p18S.7), and a deletion in ITS1 (p18S.2). All three constructs contain the hybridization tag for detection of mature 18S rRNA. Cells transfected with the various plasmids at different dilutions showed no substantial differences when compared via Northern blot (FIG. 9). Taken together, the results indicate that deletion of the flanking spacer regions does not affect translation from or assembly of mature subunits. However, this study does not rule out the possibility that the flanking regions may have more subtle effects. The results also show that a logarithmic dilution of the p18S.1 vector with filler plasmid does not produce a logarithmic decrease in the levels of mature 40S subunits, indicating that the standard conditions used in the experiments (1.0 µg plasmid) are saturating the cell's ability to express 40S ribosomal subunits.

Example 7

Materials and Methods rDNA cloning and mutagenesis: 18S rDNA and flanking regions were amplified by PCR using genomic DNA prepared from mouse N2a cells and oligonucleotide primers rDNA.1 and rDNA.2 (Table 1). Cloning into plasmid pRL-CMV (Promega) used NheI and NotI restriction sites that were introduced at the 5' ends of rDNA.1 and rDNA.2, respectively. All sequencing of PCR products and plasmid constructs was performed using standard Sanger sequencing. To detect synthetic 18S rRNAs, a 24 nt sequence was cloned into the 18S rDNA as a hybridization tag using the SacI site in expansion segment 3. The hybridization tag was generated using a random sequence generator (www.faculty.ucr.edu/~mmaduro/random.htm) and selected based on minimal predicted self-complementarity and secondary structure as determined using Oligo Calc (www.basic.northwestern.edu/biotools/OligoCalc.html). Constructs containing the hybridization tag are designated with a 'tag' extension, e.g. pPol-I (18S-tag).

A short RNA polymerase (pol-I) promoter element containing the 5' SalI-box and a minimal pol-I promoter was cloned from the intergenic spacer of a 45S rDNA gene (−169 to +1) using primers Pol-I.1 and Pol-I.2. A BlgII site in Pol-I.1 and an NheI site in Pol-I.2 were used to clone the PCR fragment into pRL-CMV, replacing the BlgII-NheI fragment which contains the CMV promoter and a chimeric intron. A pol-I terminator was obtained from the 3' external transcribed spacer (3' ETS) of 45S rDNA, which contains 10 SalI-box pol-I terminators, using primers Pol-I.3 and Pol-I.4. A NotI site in primer Pol-I.3 and an MfeI site in primer Pol-I.4 were used to clone the PCR fragment into pRL-CMV, replacing a NotI-MfeI fragment that contains the SV40 polyA signal.

Three 5' ETS and two ITS1 fragments were cloned for these studies. The 5' ETS fragments are the entire 4,014 nt sequence, and two shorter fragments that extend 1,188 and 703 nucleotides upstream of site 1. The two larger fragments were cloned using NdeI as the 3' site, which lies immediately 3' of site 1. The 4,014 nt sequence was obtained from a PCR product containing the pol-I promoter and amplified using primers rDNA.3, which contains a 5' BglII site, and rDNA.4. The 1,188 nt fragment was obtained from a PCR product amplified using primers rDNA.4 and rDNA.5, and cloned using an NheI site contained within the 5' ETS. The 703 nt fragment was cloned together with the 18S rDNA in PCR reactions performed using oligonucleotide primers rDNA.1 and rDNA.2. The two ITS1 fragments are a 1 kb fragment amplified by using primers rDNA.6 and rDNA.7, and a 70 nt fragment cloned with the 18S rDNA. The 1 kb fragment was subcloned using a NotI site that was introduced into rDNA.7 and an EcoNI site present at the 3' end of the 18S rDNA. The various fragments described above were used to generate 6 constructs. The construct containing the full-length 5' ETS was assembled using the following restriction fragment combination: MfeI-BglII-NdeI-EcoNI-NotI-MfeI. The other constructs were assembled using the restriction fragment combination: MfeI-BglII-NheI-NdeI-EcoNI-NotI-MfeI.

For transcription via the RNA polymerase II (pol-II) promoter, the inserts described above, except for the full-length 5' ETS insert, were transferred into plasmid pRL-CMV, replacing the NheI-NotI fragment. The full-length 5' ETS insert was first re-amplified using oligonucleotide rDNA.12 to introduce an NheI site at the 5' end. The chimeric intron of pRL-CMV was removed and replaced with a SacI-NheI fragment generated by annealing oligonucleotides rDNA.8 and rDNA.9.

Deletion constructs were generated by digesting plasmid pPol-I(18S-tag) with the following enzymes followed by religation: PvuII-AfeI (p18S.11), PvuII-ZraI (p18S.10), AvrII-NheI (p18S.9), XhoI-XhoI (p18S.8), and AatII (blunt)-BglI (blunt)(p18S.7). p18S.7 was generated using a partial digestion with BglI as the plasmid contains additional sites.

Mutations were generated by PCR, using complementary 45 nt primers containing the mutations and 5' and 3' flanking primers located outside of restriction enzyme sites used for cloning. A fragment from each PCR reaction was then subcloned into the expression construct; an NcoI-HindIII fragment of 18S for antibiotic resistance mutations, or an AvrII-AatII fragment of 5' ETS for 5' hinge mutations.

Reporter Genes: pGL4.13 (Promega) was used as a monocistronic control. Dicistronic controls were constructed from pGL4.13 with a double insertion 3' of the synthetic firefly luciferase gene luc2. The first fragment, an XbaI-NcoI fragment was derived from previous constructs containing a multiple cloning site (MCS), the Encephalomyocarditis virus (EMCV) internal ribosome entry site (IRES), or the poliovirus (PV) IRES (10). The second fragment was an NcoI-XbaI fragment from phRG-B (Promega), which contains the humanized *Renilla* luciferase gene hRluc.

Analysis of rRNA expression and processing: All constructs in these studies were tested in transiently transfected Neuro 2a (N2a) cells. Cells were seeded in 6 well dishes at 100,000 cells/well and transfected the next day using 1 μg DNA per well with 3 μl Fugene 6 (Roche). Approximately 48 hours post transfection, total RNA was extracted with Trizol reagent (Life Technologies). RNA was quantified and 2 μg of total RNA and indicated amounts of rRNA in vitro transcripts were electrophoresed on denaturing agarose gels for Northern blot analyses. For each set of samples, gels included a single stranded RNA marker (1 μg of ssRNA marker; NEB). The positions of the bands were marked on membranes post transfer using Ethidium Bromide staining. For Northern blot analyses, membranes were hybridized overnight at 37° C. in Ultrahyb solution (Ambion) using $^{32}$P- or $^{33}$P-5' labeled oligonucleotide probes. Blots were analyzed using a Molecular Dynamics Phosphorimager system. Different oligonucleotide probes (Table 1) were used to detect RNAs containing various sequences. The α-tag probe for RNAs containing the 24-nt hybridization tag; the α-5' ETS probe for RNAs containing 5' ETS sequences immediately upstream of site 1, the α-ITS1 probe for RNAs containing ITS1 sequences immediately 3' of the site 2 and the α-18S rRNA probe for 18S rRNA.

Size control transcripts were generated using an Ambion MEGAscript in vitro transcription kit from PCR-generated fragments amplified using plasmid templates with 5' primer rDNA.10, which contains the T7 RNA polymerase promoter fused to the first 24 nucleotides of 18S rDNA and 3' primer rDNA.11 that is complementary to nucleotides at the 3' end of the 18S rDNA. The resulting transcripts contain 3 additional 5' guanine nucleotides compared to endogenous 18S rRNAs. The untagged transcript is 1,874 nucleotides; the tagged transcript is 1,898 nucleotides.

Analysis of synthetic ribosomes: For analyses of protein expression from pactamycin-resistant ribosomes, cells were transfected in 24 well dishes seeded at 20,000 cells/well 24 hours prior to transfection. 0.5 μl DNA was transfected per well using 1.5 μA Fugene 6 (Roche). Approximately 40 hours post transfection, cell culture media was switched to starvation medium lacking L-methionine and L-cysteine. Cells were starved for 30 minutes before the media was changed to fresh starvation media containing pactamycin as indicated in the figures, cultured for an additional 30 minutes, and then labeled with $^{35}$S-Met/$^{35}$S-Cys for 4 hours using 1.2 μl of TRAN35S label (MP Biomedicals, Ohio) per well. After labeling, media was removed and cells washed with ice cold PBS. Cells were lysed on ice for 30 minutes on a rocker table with 35 μl ice cold RIPA buffer (10 mM Sodium Phosphate pH 7.3, 150 mM NaCl, 1 mM EDTA 1% IGEPAL CA-603, 0.1% SDS, 1% Sodium-Deoxycholate, and 1× complete protease inhibitor (Roche)). Cell lysates were centrifuged for 15 minutes at 12,000×g to remove debris and pellet genomic DNA; 19 μl of lysate was transferred to a new tube with 1 μl 1M DTT and 4×LDS loading buffer (Invitrogen). Samples were heated for 5 minutes at 90° C., placed on ice, and electrophoresed on 4-12% BIS-TRIS NuPage gels using MOPS-SDS buffer. Gels were soaked in 30% Methanol, 5% glycerol for 30 minutes, vacuum dried, and analyzed using a Molecular Dynamics Phosphorimager system or film.

For polysome analysis, cells were seeded at 100,000 per well in 6-well plates, and transfected 24 h later with an 18S rDNA expression plasmid using 6 μl Fugene 6 per μg DNA. Forty-eight hours post transfection, samples were processed at 4° C.; culture media was aspirated and cells washed with ice cold PBS containing 0.1 mg/ml cycloheximide. Six wells were scraped with 300 μl of cold lysis buffer A (20 mM Tris-HCl pH7.5, 15 mM MgCl$_2$, 100 mM KCl, 1% TritonX- 100, 0.1 mg/ml cycloheximide, 0.05× Murine RNase inhibitor (NEB), 1× complete protease inhibitor (Roche)). The scraped cells and lysis buffer were then transferred to tubes and incubated on ice for 10 minutes with occasional mixing for passive lysis. Tubes were centrifuged for 10 minutes at 16,000×g to pellet cellular debris. Approximately 1 $OD_{260}$ of supernatant was loaded onto a 12 ml 10%-50% sucrose gradient (20 mM Tris-HCl pH7.5, 15 mM $MgCl_2$, 100 mM KCl, 0.1 mg/ml cycloheximide). Gradients were centrifuged at 35,000 rpm (155,000×g) in a SW40Ti rotor for 3 hours, and then fractionated using an ISCO fractionator. RNA was ethanol precipitated from these fractions and the resulting pellet was extracted with phenol/chloroform. For each pooled fraction, $1/10^{th}$ of the total volume was analyzed by primer extension using ddCTP to distinguish between endogenous rRNAs and synthetic rRNAs containing the pactamycin-resistance mutation. Controls for the primer extension reactions contained 200 ng of a 1:1 18Swt/18S693mutant transcript mix (Control 1) and 600 ng N2a total RNA (Control 2). RNA sequencing ladders were generated using 200 ng of the same 1:1 transcript mix.

For EDTA-dissociated ribosomes, cells were washed 48 hours post-transfection with 1 mL warm PBS, and 18 wells were lysed using 800 µl ice cold lysis buffer B (20 mM Tris-HCl pH 7.5, 100 mM KCl, 0.3% Igepal CA-630, 0.05× Murine RNase inhibitor (NEB), 1× complete protease inhibitor (Roche)). The lysate was further processed using a dounce homogenizer (100 passes) and then spun for 15 minutes at 16,000×g to pellet debris. The $OD_{260}$ of each lysate supernatant was determined and 1/5th volume of EDTA buffer (20 mM Tris-HCl pH 7.5, 100 mM KCl, 150 mM EDTA, 0.05× Murine RNase inhibitor (NEB), 1× complete protease inhibitor (Roche)) was added to adjust the final concentration of EDTA to 30 mM. Approximately 4.5 $OD_{260}$ of each lysate was loaded onto a 12 mL 10-35% sucrose gradient in 20 mM Tris-HCl pH 7.5, 100 mM KCl, 30 mM EDTA. Gradients were spun for 5 hours in an SW40Ti rotor at 40,000 rpm (200,000×g). RNAs from fractionated samples were analyzed as described above except $1/60^{th}$ of each pooled fraction was used due to more efficient lysis and concentration of ribosomal subunits.

P100 pellet and S100 supernatant fractions were prepared using mild lysis conditions to minimize lysis of nuclei. Forty-eight hours post transfection, plates were washed with 1 ml warm PBS, 250 µl ice cold lysis buffer B with 5 mM $MgCl_2$ and 2 mM DTT was then added to each well. As described above, wells were scraped; the lysate was subjected to active lysis and centrifuged to pellet debris. The supernatants were then centrifuged for 3 hours at 100,000×g. RNA was isolated from supernatants as described for fractions above. The P100 pellet was softened overnight with 20 mM Tris pH 7.5, 100 mM KCl, 5 mM $MgCl_2$ and RNA was extracted with phenol/chloroform.

For cotransfection experiments using 18S rDNA and luciferase reporter constructs, cells were seeded in 6-well plates and transfected with an 18S rDNA expression construct, as described above using 1 µg vector:3 µl Fugene 6 per well. For pactamycin treatment, cell media was removed 48 hours post transfection, and replaced with media containing 100 ng/ml pactamycin. Cells were cultured for ≈30 minutes and then transfected with reporter constructs using 1 µg plasmid and 2 µl Lipofectamine 2000 (Invitrogen). Cells were cultured overnight, washed with warm PBS, and lysed with passive lysis buffer (Promega). For each independent transfection experiment, an equal volume of cell lysate (20 µl out of 250 µl) was assayed using an E&G Berthold 96 well format dual injector luminometer.

While this specification contains many specifics, these should not be construed as limitations on the scope of the subject matter that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Only a few examples and implementations are disclosed. Variations, modifications and enhancements to the described examples and implementations and other implementations may be made based on what is disclosed.

All publications, databases, GenBank sequences, patents, and patent applications cited in this specification are herein incorporated by reference as if each was specifically and individually indicated to be incorporated by reference.

What is claimed is:

1. A synthetic and isolated polynucleotide encoding a mammalian 18S rRNA that is resistant to pactamycin, wherein the pactamycin-resistance is conferred by one or more single residue substitutions in the 18S rRNA sequence, wherein the one or more single residue substitutions is at a position corresponding to G963, A964, C1065 or C1066 of mouse 18S rRNA (SEQ ID NO:23); a fragment thereof harboring said substitutions; a fully complementary sequence thereto; or a substantially identical sequence of the foregoing.

2. The polynucleotide of claim 1, wherein the single residue substitution is at a position corresponding to position G963 of SEQ ID NO:23.

3. The polynucleotide of claim 1, wherein the single residue substitution corresponds to a G963A substitution in SEQ ID NO:23.

4. The polynucleotide of claim 1, wherein the polynucleotide encodes human 18S rRNA or mouse 18S rRNA.

5. The polynucleotide of claim 1, wherein the polynucleotide comprises SEQ ID NO:23 except for a G963A substitution.

6. A mammalian 18S rRNA encoded by the polynucleotide of claim 1.

7. An expression vector expressing the polynucleotide of claim 1.

8. The vector of claim 7, wherein the polynucleotide further comprises the 5' ETS and ITS1 of the rDNA sequence.

9. The vector of claim 7, further comprises a pol-I promoter or a cytomegalovirus (CMV) promoter.

10. The vector of claim 7, further comprises the 3' ETS or an SV40poly(A) signal.

11. An isolated host cell harboring the expression vector of claim 7.

12. A kit comprising the expression vector of claim 7.

13. A kit comprising an isolated cell containing the expression vector of claim 7.

14. A method for preferentially translating a recombinant mRNA, the method comprising:
   expressing the synthetic polynucleotide of claim 1 in a mammalian cell, wherein the synthetic polynucleotide has been altered to introduce one or more mutations that confer preferential binding of the 18S rRNA to the recombinant mRNA;
   providing the recombinant mRNA to the cell; and
   exposing the cell to pactamycin in an amount sufficient to reduce or eliminate protein synthesis from the cell's endogenous 40S ribosomal subunits, thereby largely restricting protein synthesis in the cell to 40S ribosomal subunits comprising the 18S rRNA expressed by the synthetic polynucleotide of claim 1 and preferentially translating the recombinant mRNA.

15. A method for identifying a mutation in 18S rRNA that alters ribosomal functions, comprising:
   (a) introducing an additional mutation to the synthetic polynucleotide of claim 1;
   (b) expressing the synthetic polynucleotide bearing the additional mutation in a host cell in the presence of pactamycin; and
   (c) detecting an alteration in the ribosomes of the host cell relative to that of a control cell expressing the synthetic polynucleotide without the additional mutation; thereby identifying the additional mutation as one altering ribosomal functions.

16. The method of claim 15, wherein the synthetic polynucleotide is present in an expression vector introduced into the host cell.

17. The method of claim 15, wherein the single residue substitution corresponds to a G963A substitution in SEQ ID N0:23.

18. The method of claim 15, wherein the synthetic polynucleotide comprises SEQ ID N0:23 except for a G963A substitution.

19. A method for producing ribosomes with enhanced translation efficiency in a mammalian cell, comprising:
   (a) introducing an additional mutation to the synthetic polynucleotide of claim 1;
   (b) introducing the synthetic polynucleotide bearing said additional mutation into a host mammalian cell;
   (c) culturing the cell in the presence of pactamycin; and
   (d) detecting enhanced translation efficiency in the cell relative to that of a control cell expressing the synthetic polynucleotide without the additional mutation; thereby producing ribosomes with enhanced translation efficiency.

20. The method of claim 19, wherein the synthetic polynucleotide is present in an expression vector introduced into the host cell.

21. The method of claim 19, wherein the single residue substitution corresponds to a G963A substitution in SEQ ID NO:23.

22. The method of claim 19, wherein the synthetic polynucleotide comprises SEQ ID NO:23 except for a G963A substitution.

23. The method of claim 19, wherein translation efficiency is determined by measuring the level of a specific polypeptide in the host cell.

\* \* \* \* \*